US007534930B2

(12) United States Patent
Vishnevetsky et al.

(10) Patent No.: US 7,534,930 B2
(45) Date of Patent: May 19, 2009

(54) TRANSGENIC DISEASE RESISTANT BANANA

(75) Inventors: Jane Vishnevetsky, Rehovot (IL); Moshe Flaishman, Herzlia (IL); Yuval Cohen, Petach-Tikva (IL); Igal Elad, Givat Shmuel (IL); Margarita Velcheva, Nes Ziona (IL); Uri Hanania, Holon (IL); Avi Perl, Rishon-LeZion (IL)

(73) Assignee: The State of Israel - Ministry of Agriculture & Rural Development, Beit-Dagan (IL)

( * ) Notice: Subject to any disclaimer, the term of this patent is extended or adjusted under 35 U.S.C. 154(b) by 0 days.

(21) Appl. No.: 11/430,924

(22) Filed: May 10, 2006

(65) Prior Publication Data
US 2006/0288446 A1    Dec. 21, 2006

Related U.S. Application Data

(63) Continuation-in-part of application No. PCT/IL2004/001032, filed on Nov. 11, 2004.

(60) Provisional application No. 60/574,235, filed on May 26, 2004, provisional application No. 60/519,654, filed on Nov. 14, 2003.

(51) Int. Cl.
*A01H 1/00* (2006.01)
*C12N 15/82* (2006.01)
*C12N 15/87* (2006.01)
*C07H 21/04* (2006.01)

(52) U.S. Cl. .................... 800/279; 800/278; 536/23.74; 536/23.6

(58) Field of Classification Search ........................ None
See application file for complete search history.

(56) References Cited

U.S. PATENT DOCUMENTS

| | | | |
|---|---|---|---|
| 4,017,192 | A | 4/1977 | Rosenthal |
| 5,991,028 | A | 11/1999 | Cabib et al. |
| 6,007,996 | A | 12/1999 | McNamara et al. |
| 6,020,129 | A | 2/2000 | Schröder et al. |
| 6,087,560 | A * | 7/2000 | Cornelissen et al. ........ 800/301 |
| 6,631,203 | B2 | 10/2003 | Ellis et al. |
| 6,697,509 | B2 | 2/2004 | De La Torre-Bueno |
| 6,718,053 | B1 | 4/2004 | Ellis et al. |
| 6,920,239 | B2 | 7/2005 | Douglass et al. |
| 6,933,378 | B2 * | 8/2005 | Atabekov et al. .......... 536/24.1 |

FOREIGN PATENT DOCUMENTS

| | | | |
|---|---|---|---|
| WO | WO 95/02319 | | 1/1995 |
| WO | WO 00/01812 | * | 3/2000 |
| WO | WO 2005/047515 | | 5/2005 |

OTHER PUBLICATIONS

Perl et al. 1993, Theor. Appl. Genet. 85:568-576.*
Kobayashi et al. 2000, GenBank Accession No. AB046375.*
Jeandet et al. 2002, J. Agric. Food Chem. 50:2731-2741.*
Collinge et al. 1993, The Plant J. 3;31-40.*
Laitakari "Computer-Assisted Quantitative Image Analysis of Cell Proliferation, Angiogenesis and Stromal Markers in Experimental and Laryngeal Tumor Development", Acta Uiv,Oulu, D 713, 104 pages, 2003. Academic Dissertation.
Cook et al. "A Nationwide Survey of Observer Variation in the Diagnosis of Thin Cutaneous Malignant Melanoma Including the MIN Terminology", Journal of Clinical Pathology, 50: 202-205, 1997.
Braun-Falco et al. "Histopathological Characteristics of Small Diameter Melanocytic Neavi", Journal of Clinical Pathology, 56: 456-464, 2003.
Huang et al. "From Quantitative Microscopy to Automated Image Understanding", Journal of Biomedical Optics, 9(5): 893-912, 2004.
Garcia-Olmedo et al. "Plant Proteinaceous Inhibitors of Proteinases and Alpha-Amylases", Oxford Surveys of Plant Molecular & Cell Biology, 4: 275-334, 1987.
Jones et al. "The Role of Leucine-Rich Repeat Proteins in Plant Defences", Advances in Botanical Research Incorporating Advances in Plant Pathology, 24: 89-167, 1997.
Moreno et al. "A Lectin Gene Encodes the Alpha-Amylase Inhibitor of the Common Bean", Proc. Natl. Acad. Sci. USA, 86: 7885-7889, 1989.
Linthorst et al. "Analysis of Gene Families Encoding Acidic and Basic Beta-1,3-Glucanase of Tobacco", Proc. Natl. Acad. Sci. USA, 87: 8756-8760, 1990.
Vigers et al. "A New Family of Plant Antifungal Proteins", Molecular Plant-Microbe Interactions, 4(4): 315-323, 1991.
Leah et al. "Biochemical and Molecular Characterization of Three Barley Seed Proteins With Antifungal Properties", The Journal of Biological Chemistry, 266(3): 1564-1573, 1991.
Christoffersen et al. "Cellulase Gene Expression in Ripening Avocado Fruit: The Accumulation of Cellulase mRNA and Protein as Demonstrated by cDNA Hybridization and Immunodetection", Plant Molecular Biology, 3: 385-391, 1984.

(Continued)

*Primary Examiner*—Stuart F Baum
*Assistant Examiner*—Li Zheng

(57) ABSTRACT

A nucleic acid construct or construct system which includes (i) a first polynucleotide encoding endochitinase, (ii) a second polynucleotide encoding stilbene synthase and (iii) a third polynucleotide encoding superoxide dismutase. In addition, banana cells transformed with the nucleic acid construct or construct system, banana plants generated therefrom and methods of producing same.

6 Claims, 11 Drawing Sheets
(8 of 11 Drawing Sheet(s) Filed in Color)

OTHER PUBLICATIONS

Collinge et al. "Plant Chitinases", The Plant Journal, 3(1): 31-40, 1993.

Payne et al. "Evidence for A Third Structural Class of Beta-1,3-Glucanase in Tobacco", Plant Molecular Biology, 15: 797-808, 1990.

Bol et al. "Plant Pathogenesis-Related Proteins Induced by Virus Infection", Annual Reviews in Phytopathology, 28: 113-138, 1990.

Bohlmann et al. "Leaf-Specific Thionins of Barley—A Novel Class of Cell Wall Proteins Toxic to Plant-Pathogenic Fungi and Possibly Involved in the Defence Mechanism of Plants", The EMBO Journal, 7(6): 1559-1565, 1988.

Mindrinos et al. "The A. Thaliana Disease Resistance Gene RPS2 Encodes A Protein Containing A Nucleotide-Binding Site and Leucine-Rich Repeats", Cell, 78: 1089-1099, 1994.

Ward et al. "Differential Regulation of Beta-1,3-Glucanase Messenger RNAs in Response to Pathogen Infection", Plant Physiology, 96: 390-397, 1991.

Tucker et al. "Bean Abscission Cellulase. Characterization of A cDNA Clone and Regulation of Gene Expression by Ethylene and Auxin", Plant Physiology, 88: 1257-1262, 1988.

Song et al. "A Receptor Kinase-Like Protein Encoded by the Rice Disease Resistance Gene, Xa21", Science, 270: 1804-1806, 1995.

Bent et al. "RPS2 of *Arabidopsis Thaliana*: A Leucine-Rich Repeat Class of Plant Disease Resistance Genes", Science, 265: 1856-1860, 1994.

Grant et al. "Structure of the Arabidopsis RPM1 Gene Enabling Dual Specificity Disease Resistance", Science, 269: 843-846, 1995.

Johal et al. "Reductase Activity Encoded by the HM1 Disease Resistance Gene in Maize", Science, 258: 985-987, 1992.

Martin et al. "Map-Based Cloning of A Protein Kinase Gene Conferring Disease Resistance in Tomato", Science, 262: 1432-1436, 1993.

Chakrabarti et al. "MSI-99 Magainin Analogue, Imparts Enhanced Disease Resistance in Transgenic Tobacco and Banana", Planta, 216: 587-596, 2003.

Perl et al. "Enhanced Oxidative-Stress Defense in Transgenic Potato Expressing Tomato Copper, Zinc Superoxide Dismutases", Theoretical and Applied Genetics, 85(5): 568-576, 1993.

\* cited by examiner

Fig. 2A
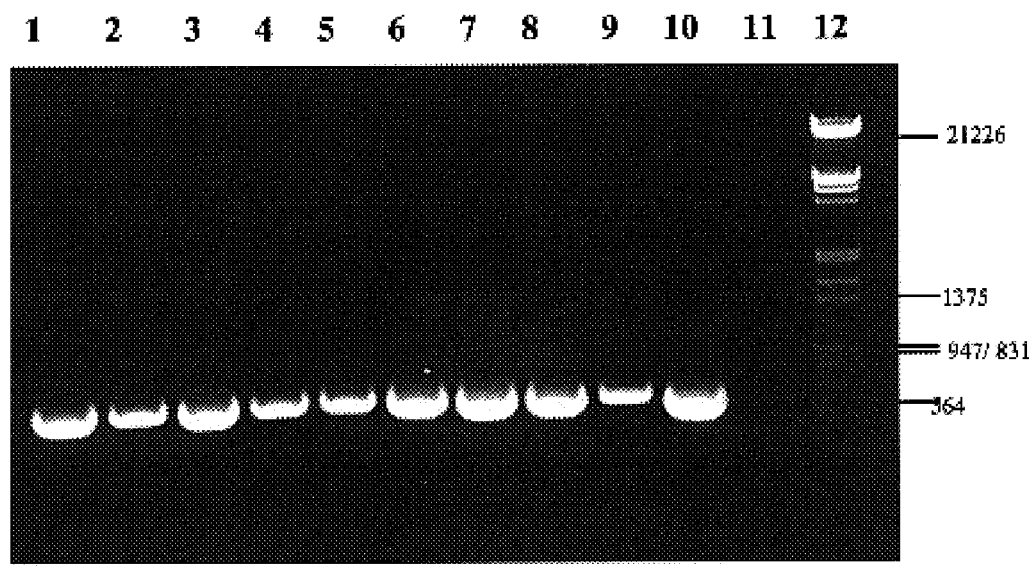
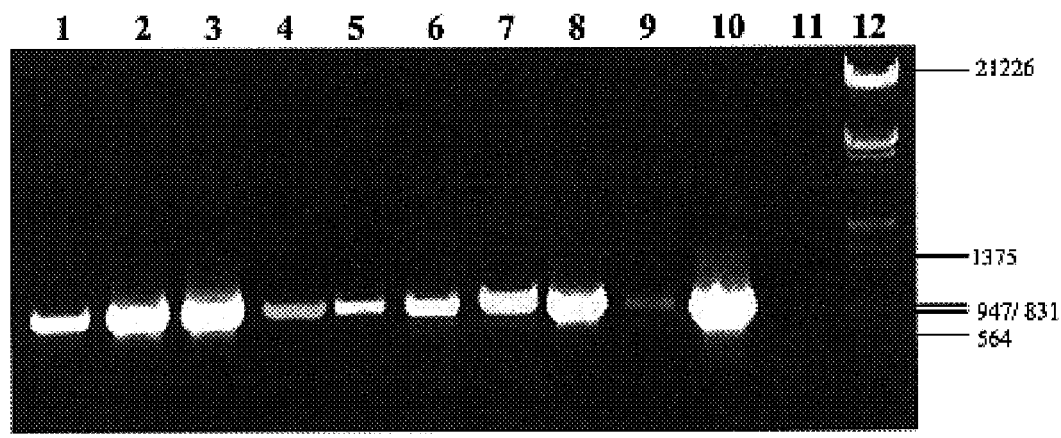
Fig. 2B

SEQUENCE LISTING

<160> NUMBER OF SEQ ID NOS: 13

<210> SEQ ID NO 1
<211> LENGTH: 1554
<212> TYPE: DNA
<213> ORGANISM: Trichoderma harzianum

<400> SEQUENCE: 1

```
gctcttttca gcagcaactt cttccttca aagcatctct tgacaacctt tgctgaatct      60
caaacacttc accatgttgg gcttcctcgg aaaatccgtg gccctgcttg ctgcgctgca    120
ggccactctc atttctgcat ctcctgtaac tgcaaacgac gtctctgttg agaagagagc    180
```

| | |
|---|---:|
| cagtggatac gcaaacgccg tctacttcac caactggggt atttacggcc gcaacttcca | 240 |
| gcctcagaac ctggtcgcgt cggacatcac tcatgtcatc tactcgttca tgaacttcca | 300 |
| agcagacggc actgtcgtct ctggagatgc ctacgccgat tatcagaagc actatgacga | 360 |
| cgattcttgg aacgacgtcg gtaacaatgc gtacggctgt gtgaagcagc tgttcaagct | 420 |
| gaagaaggcc aaccgcaact tgaaggttat gctttccatc ggtggctgga cctggtccac | 480 |
| caactttcct tctgcagcaa gcaccgatgc caaccgcaag aactttgcca agactgccat | 540 |
| caccttcatg aaggactggg gtttcgatgg tattgacgtc gattgggagt accccgccga | 600 |
| tgatacccag gccaccaaca tggttcttct gctcaaggag atccgatctc agctagatgc | 660 |
| ctatgctgcg caatacgctc cgggctacca cttccttctt tccattgctg ccccgctgg | 720 |
| cccagagcac tactctttcc tgcacatgtc cgaccttggc caagttctcg actatgtcaa | 780 |
| cctcatggcc tacgactatg ctggttcttg gagcagctac tccggacacg atgccaactt | 840 |
| gtttgccaac ccgtccaacc ccaactcttc accatacaac accgatcaag ctatcaagga | 900 |
| ctatatcaag ggaggtgttc ccgcaagcaa gatcgttctt ggcatgccca tctacggacg | 960 |
| agcttttgag agcaccggtg gcattggcca gacctacagt ggaattggat ctggaagctg | 1020 |
| ggagaacggt atttgggact acaaggttct tcccaaggcc ggcgccacag tccagtatga | 1080 |
| ctctgtcgca caggcatact acagctatga ccccagcagc aaggagctca tctcttttcga | 1140 |
| taccccctgac atgatcaaca ccaaggtctc ttacctcaag aacctcggcc tgggaggcag | 1200 |
| catgttctgg gaagcttctg ctgacaagac tggctctgac tccttgatcg aacaagcca | 1260 |
| cagagctttg ggaagcctag actccactca gaacttgctg agctacccca actcccagta | 1320 |
| tgataacatc cgaagcggtc tcaactagag atctttcttc ttcttatctt tttctttttac | 1380 |
| ttcccctatg gttgtaccaa catttcacac acgttatgcg aaacgattat gcagggagcg | 1440 |
| ttatttttta gtaaatagtt gcccttttgag atatatgaac ctgtacataa agaactacta | 1500 |
| gcagtatata aggagacatg caggatctct agaattgact tccatgcttt cctc | 1554 |

<210> SEQ ID NO 2
<211> LENGTH: 1549
<212> TYPE: DNA
<213> ORGANISM: Vitis sp.

<400> SEQUENCE: 2

| | |
|---|---:|
| atggaggatc cggcttcaat tgaggaaatt agaaacgctc aacgtgccaa gggtccggcc | 60 |
| accatcctag ccattggcac agctactccc gaccactgtg tctaccagtc tgattatgct | 120 |
| gattactatt tcagagtcac taagagcgag cacatgactg agttgaagaa gaagttcaat | 180 |
| cgcatatgta agtatatata ttcatgcatt aattcttaca ttcacaacat ttctatacat | 240 |
| atacgagtgt gctattaagt gagggtcacc tccaagtgaa tgaatgtttc aagcttagag | 300 |
| aatagctttt agctaaatta cttaaggaaa cttgaaaatc attttacatc agtaaccgat | 360 |
| attcctttca tttgattgta agggcttgaa gagctgttct ttgaatcatg tagcattgct | 420 |
| agctataatt aagaataacc ttttataatt tcttcaatgt aaatgcatg ttgatcatct | 480 |
| tcaagaatat actatatgac tagtcgttgg aaaactaatg tgttcatctt atttcttta | 540 |
| cagggtgaca aatcaatgat caagaagcgt acattcatt tgaccgaaga aatgcttgag | 600 |
| gagcacccaa acattggtgc ttatatggct ccatctctca acattacgcc aagagattat | 660 |
| cactgctgag gtacctaaac ttggtaaaga agcagcattg aaggctctta agaatgggg | 720 |
| tcaaccaaag tccaagatca cccattcttg tatttttgtac aacctccggt gtagaaatgc | 780 |

```
ccggtgcaga ttacaaactc gctaatctct taggccttga acatcggtt  agaagggtga    840 tcttgtacca tcaaggttgc tatgcaggtg gaactgtcct tcgaactgct aaggatcttg    900
cagaaaataa cgcaggagca cgagttcttg tggtgtgctc tgagatcact gttgttacat    960
ttcgtgggcc ttccgaagat gctttggact ctttagttag gtcaagccct ttttggtgat   1020
gggtcagcag ctgtgattgt tggatcagat ccagatgtct ccattgaacg acccctcttc   1080
caacttgttt cagcagcaca acgtttatt  cctaattcag caggtgctat gcgggtaac    1140 ttacgtgagg tgggactcac ctttcacttg tggcctaatg tgcctacttt gatttccgag   1200
aacatagaga atgcttgaa  tcaggctttt gacccacttg gtattagcga ttggaactcg   1260
ttattttgga ttgctcaccc tggtggccct gcaattcttg atgcagttga agcaaaactc   1320
aatttagaga aaagaaact  tgaagcaaca aggcatgtgt taagtgagta tggtaacatg   1380
tctagtgcat gtgtctttgt ttattttgga tgagatgaga agaaatccc  taaagggga    1440 aaaagctatc cacaggtgac ggattggatt ggggtacta  ttcggttttg ggccaggctt   1500
gaccattgag accgttgtgc tgcatagcgt tcctatggtt acaaattga                1549

<210> SEQ ID NO 3
<211> LENGTH: 777
<212> TYPE: DNA
<213> ORGANISM: Lycopersicon esculentum

<400> SEQUENCE: 3
caaaaatggt gaaggccgtc gccgtcctta acagcagtga aggtgttagt ggcacctacc     60
tcttcactca agtaggagta gctccaacca cagttaatgg aaatatttct ggcctaaaac    120
ctggacttca tggcttccat gtccatgccc ttggtgatac cacaaatggc tgtatgtcaa    180
caggaccaca ttacaatcct gctggtaagg agcatggtgc tcctgaagat gaggtgcgtc    240
atgctggtga tcttggtaac atcacagttg agaagatgg  tactgcatct tttactatta    300
ccgacaagca gattcctctc actggtccac agtccatcat ggaagagct  gttgttgttc    360 atgctgatcc tgatgatctt ggaaagggag gacatgagct cagtaaaagc accggaaatg    420
ctggcggaag gattgcttgt ggtattattg gcctccaggg ttaactgctc cggtgaggtg    480
aagattcagc aactagcggt ggtgtctgtc ttagaataaa gttatattgg agctgctgag    540
ccttgttttc tatgtatttta tcatttgacg ccttttgaat tggggttgaa ccattcataa    600
tacatgactg tagtgctgct tttcagtgga tgttgtacta gttttgccg  atcattaacc    660 ataaaaaaac agggctgtgt tagctttgct ggtttcttaa atttgagtgg atggtttgaa    720
aactagacaa aatttagatg aatttgcaga ttacagtgcc tgcagttttt gttcata       777

<210> SEQ ID NO 4
<211> LENGTH: 1399
<212> TYPE: DNA
<213> ORGANISM: Pisum sativum

<400> SEQUENCE: 4
gaattcttca aaaaaaagt  tgcccttgag aaactaataa gttaataaac taagacctct     60
aaaaaaaaag ttaataaact aatatgaata ttctctaaac aaaaaataaa actaagaaga    120
atatattttg cttatttacc agaaaaatac tttgcttagt caaaagaaga agaatattgt    180
gaattaattt gatactgatg attttttaaag ctgtagatat ttacgtatt  agttaaaaaa    240 atacaattat tatatatttta attggtgtgt ctattcaagt gtttaactta agttgaggtt    300
```

-continued

```
tattcttatg ttactaagtt ggagtggaga agaagactat ttgcttggga ggaggaacgc      360
ccagtagaat gtgttattat tttttatttt tttgtaagga gtagagtgtg ttatgttgct      420
tgaataattt ttttttgtag gataatgtat tagacaaata aatttggaaa cacgaccctg      480
tcaaagagta cacggtaaag ggggtggtat acaaagagt gcgtcgctct attcttcagg       540
tcatttggtt tgctacagtt taggaaattt gggaggaaag aaataacaga ctgtataacg      600
tcaaagaatg ctcggttatt caggtggtag ataagattaa gtttcttgct tttgcatggg      660
tgaaggcaaa gtttgcttct cttccattca attaccatgg gtggcggctt agtccgttta      720
ccatactgga cataggctaa gagttttctt tttctcgttt ttccattaca agttctttat      780
gtaaatactg ttttgacttt ggtgttcttc ccttagtaca ccttgtgcta ggaaggacta      840
ttttgatttg gtaatatatt tcatttaac ctcttaaaaa aaaatcagga aagaaaaag        900 ataaaggtcg gaagtgttac ctgattataa aataaatgat taaattgaaa ataaagataa     960
ataactaaaa tgttttctat aattaagtta agagatgaaa tatgtaattt tcccaattat     1020
atattatgta agttttatt tattttatat acgttgtttt gctttgaaat ttgagtggtc     1080
ttggaggaga gaaaaacaaa agagaaaaga aaaattaata gtagatgcaa taattttgtt     1140
agtccaaata ataatatagt tttctttaaa aataatatca tccaaactca tacattaaaa     1200
atattattca aatttatgtc acgtcacaat gagaaaaaat ggcccaacga ccttgtatta     1260
cacatcatcg tcatcatcat ctaaagtcta aacaatacat cttcttttcc tataaataca     1320
agactcaact ccactcataa atcacacagg caaacaatta acttcttaat agtttgttat     1380
ttcacacatt aggggccag                                                  1399
```

<210> SEQ ID NO 5
<211> LENGTH: 1993
<212> TYPE: DNA
<213> ORGANISM: Vitis sp.
<220> FEATURE:
<221> NAME/KEY: misc_feature
<222> LOCATION: (1)..(1)
<223> OTHER INFORMATION: n is a, c, g, or t

<400> SEQUENCE: 5

```
nctgcagtgc agcgtgaccc ggtcgtgccc ctctctagag ataatgagca ttgcatgtct       60
aagttataaa aaattaccac atattttttt tgtcacactt gtttgaagtg cagtttatct     120
atctttatac atatatttaa acttactct acgaataata taatctatag tactacaata      180
atatcagtgt tttagagaat catataaatg aacagttaga catggtctaa aggacaattg     240
agtattttga caacaggact ctacagtttt atcttttag tgtgcatgtg ttctcctttt      300
tttttgcaaa tagcttcacc tatataatac ttcatccatt ttattagtac atccatttag     360
ggtttagggt taatggtttt tatagactaa tttttttagt acatctattt tattctattt      420
tagcctctaa attaagaaaa ctaaaactct attttagttt ttttatttaa taatttagat     480
ataaaataga ataaaataaa gtgactaaaa attaaacaaa tacccttaa gaaattaaaa      540 aaactaagga aacatttttc ttgtttcgag tagataatgc cagcctgtta aacgccgtcg     600
acgagtctaa cggacaccaa ccagcgaacc agcagcgtcg cgtcgggcca agcgaagcag     660
acggcacggc atctctgtcg ctgcctctgg acccctctcg agagttccgc tccaccgttg     720
gacttgctcc gctgtcggca tccagaaatt gcgtggcgga gcggcagacg tgagccggca     780
cggcaggcgg cctcctcctc ctctcacggc acggcagcta cggggattc ctttcccacc      840 gctccttcgc tttcccttcc tcgcccgccg taataaatag acacccccctc cacaccctct     900
```

-continued

```
ttccccaacc tcgtgttgtt cggagcgcac acacacacaa ccagatctcc cccaaatcca      960
cccgtcggca cctccgcttc aaggtacgcc gctcgtcctc cccccccccc cctctctacc     1020
ttctctagat cggcgttccg gtccatggtt agggcccggt agttctactt ctgttcatgt     1080
ttgtgttaga tccgtgtttg tgttagatcc gtgctgctag cgttcgtaca cggatgcgac     1140
ctgtacgtca gacacgttct gattgctaac ttgccagtgt ttctctttgg ggaatcctgg     1200
gatggctcta gccgttccgc agacgggatc gatttcatga ttttttttgt ttcgttgcat     1260
agggtttggt ttgccccttt cctttatttc aatatatgcc gtgcacttgt ttgtcgggtc     1320
atcttttcat gcttttttt gtcttggttg tgatgatgtg gtctggttgg gcggtcgttc     1380
tagatcggag tagaattctg tttcaaacta cctggtggat ttattaattt tggatctgta     1440
tgtgtgtgcc atacatattc atagttacga attgaagatg atggatggaa atatcgatct     1500
aggataggta tacatgttga tgcgggtttt actgatgcat atacagagat gcttttttgtt   1560 cgcttggttg tgatgatgtg gtgtggttgg gcggtcgttc attcgttcta gatcggagta     1620
gaatactgtt tcaaactacc tggtgtattt attaattttg gaactgtatg tgtgtgtcat     1680
acatcttcat agttacgagt ttaagatgga tggaaatatc gatctaggat aggtatacat     1740
gttgatgtgg gttttactga tgcatataca tgatggcata tgcagcatct attcatatgc     1800
tctaaccttg agtacctatc tattataata aacaagtatg ttttataatt attttgatct     1860
tgatatactt ggatgatggc atatgcagca gctatatgtg gattttttta gccctgcctt     1920
catacgctat ttatttgctt ggtactgttt cttttgtcga tgctcaccct gttgtttggt     1980
gttacttctg cag                                                         1993
```

<210> SEQ ID NO 6
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 6

```
gccgcttggg tggagaggct at                                                22
```

<210> SEQ ID NO 7
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 7

```
gaggaagcgg tcagcccatt c                                                 21
```

<210> SEQ ID NO 8
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 8

```
tgggatcatg gcttcagtcg aggaaattag aaacgc                                 36
```

<210> SEQ ID NO 9
<211> LENGTH: 29
<212> TYPE: DNA

<213> ORGANISM: Artificial sequence
<220> FEATURE:
<223> OTHER INFORMATION: Single strand DNA oligonucleotide

<400> SEQUENCE: 9
cttaatttgt caccatagga atgctatgc                                29

<210> SEQ ID NO 10
<211> LENGTH: 392
<212> TYPE: PRT
<213> ORGANISM: Vitis sp.

<400> SEQUENCE: 10

```
Met Ala Ser Val Glu Glu Phe Arg Asn Ala Gln Arg Ala Lys Gly Pro
1               5                   10                  15

Ala Thr Ile Leu Ala Ile Gly Thr Ala Thr Pro Asp His Cys Val Tyr
            20                  25                  30

Gln Ser Asp Tyr Ala Asp Tyr Tyr Phe Arg Val Thr Lys Ser Glu His
        35                  40                  45

Met Thr Glu Leu Lys Lys Lys Phe Asn Arg Ile Cys Asp Lys Ser Met
50                  55                  60

Ile Lys Lys Arg Tyr Ile His Leu Thr Glu Glu Met Leu Glu Glu His
65                  70                  75                  80

Pro Asn Ile Gly Ala Tyr Met Ala Pro Ser Leu Asn Ile Arg Gln Glu
                85                  90                  95

Ile Ile Thr Ala Glu Val Pro Arg Leu Gly Arg Asp Ala Ala Leu Lys
            100                 105                 110

Ala Leu Lys Glu Trp Gly Gln Pro Lys Ser Lys Ile Thr His Leu Val
        115                 120                 125

Phe Cys Thr Thr Ser Gly Val Glu Met Pro Gly Ala Asp Tyr Lys Leu
130                 135                 140

Ala Asn Leu Leu Gly Leu Glu Thr Ser Val Arg Arg Val Met Leu Tyr
145                 150                 155                 160

His Gln Gly Cys Tyr Ala Gly Gly Thr Val Leu Arg Thr Ala Lys Asp
                165                 170                 175

Leu Ala Glu Asn Asn Ala Gly Ala Arg Val Leu Val Val Cys Ser Glu
            180                 185                 190

Ile Thr Val Val Thr Phe Arg Gly Pro Ser Glu Asp Ala Leu Asp Ser
        195                 200                 205

Leu Val Gly Gln Ala Leu Phe Gly Asp Gly Ser Ser Ala Val Ile Val
210                 215                 220

Gly Ser Asp Pro Asp Val Ser Ile Glu Arg Pro Leu Phe Gln Leu Val
225                 230                 235                 240

Ser Ala Ala Gln Thr Phe Ile Pro Asn Ser Ala Gly Ala Ile Ala Gly
                245                 250                 255

Asn Leu Arg Glu Val Gly Leu Thr Phe His Leu Trp Pro Asn Val Pro
            260                 265                 270

Thr Leu Ile Ser Glu Asn Ile Glu Lys Cys Leu Thr Gln Ala Phe Asp
        275                 280                 285

Pro Leu Gly Ile Ser Asp Trp Asn Ser Leu Phe Trp Ile Ala His Pro
290                 295                 300

Gly Gly Pro Ala Ile Leu Asp Ala Val Glu Ala Lys Leu Asn Leu Glu
305                 310                 315                 320

Lys Lys Lys Leu Glu Ala Thr Arg His Val Leu Ser Glu Tyr Gly Asn
                325                 330                 335
```

```
Met Ser Ser Ala Cys Val Leu Phe Ile Leu Asp Glu Met Arg Lys Lys
            340                 345                 350

Ser Leu Lys Gly Glu Lys Ala Thr Thr Gly Glu Gly Leu Asp Trp Gly
        355                 360                 365

Val Leu Phe Gly Phe Gly Pro Gly Leu Thr Ile Glu Thr Val Val Leu
    370                 375                 380

His Ser Val Pro Thr Val Thr Asn
385                 390

<210> SEQ ID NO 11
<211> LENGTH: 152
<212> TYPE: PRT
<213> ORGANISM: Lycopersicon esculentum

<400> SEQUENCE: 11

Met Val Lys Ala Val Ala Val Leu Asn Ser Glu Gly Val Ser Gly
1               5                   10                  15

Thr Tyr Leu Phe Thr Gln Val Gly Val Ala Pro Thr Thr Val Asn Gly
            20                  25                  30

Asn Ile Ser Gly Leu Lys Pro Gly Leu His Gly Phe His Val His Ala
        35                  40                  45

Leu Gly Asp Thr Thr Asn Gly Cys Met Ser Thr Gly Pro His Tyr Asn
    50                  55                  60

Pro Ala Gly Lys Glu His Gly Ala Pro Glu Asp Glu Val Arg His Ala
65                  70                  75                  80

Gly Asp Leu Gly Asn Ile Thr Val Gly Glu Asp Gly Thr Ala Ser Phe
                85                  90                  95

Thr Ile Thr Asp Lys Gln Ile Pro Leu Thr Gly Pro Gln Ser Ile Ile
            100                 105                 110

Gly Arg Ala Val Val Val His Ala Asp Pro Asp Asp Leu Gly Lys Gly
        115                 120                 125

Gly His Glu Leu Ser Lys Ser Thr Gly Asn Ala Gly Gly Arg Ile Ala
    130                 135                 140

Cys Gly Ile Ile Gly Leu Gln Gly
145                 150

<210> SEQ ID NO 12
<211> LENGTH: 424
<212> TYPE: PRT
<213> ORGANISM: Trichoderma harzianum

<400> SEQUENCE: 12

Met Leu Gly Phe Leu Gly Lys Ser Val Ala Leu Leu Ala Ala Leu Gln
1               5                   10                  15

Ala Thr Leu Ile Ser Ala Ser Pro Val Thr Ala Asn Asp Val Ser Val
            20                  25                  30

Glu Lys Arg Ala Ser Gly Tyr Ala Asn Ala Val Tyr Phe Thr Asn Trp
        35                  40                  45

Gly Ile Tyr Gly Arg Asn Phe Gln Pro Gln Asn Leu Val Ala Ser Asp
    50                  55                  60

Ile Thr His Val Ile Tyr Ser Phe Met Asn Phe Gln Ala Asp Gly Thr
65                  70                  75                  80

Val Val Ser Gly Asp Ala Tyr Ala Asp Tyr Gln Lys His Tyr Asp Asp
                85                  90                  95

Asp Ser Trp Asn Asp Val Gly Asn Asn Ala Tyr Gly Cys Val Lys Gln
            100                 105                 110
```

```
Leu Phe Lys Leu Lys Lys Ala Asn Arg Asn Leu Lys Val Met Leu Ser
        115                 120                 125

Ile Gly Gly Trp Thr Trp Ser Thr Asn Phe Pro Ser Ala Ala Ser Thr
130                 135                 140

Asp Ala Asn Arg Lys Asn Phe Ala Lys Thr Ala Ile Thr Phe Met Lys
145                 150                 155                 160

Asp Trp Gly Phe Asp Gly Ile Asp Val Asp Trp Glu Tyr Pro Ala Asp
                165                 170                 175

Asp Thr Gln Ala Thr Asn Met Val Leu Leu Leu Lys Glu Ile Arg Ser
            180                 185                 190

Gln Leu Asp Ala Tyr Ala Ala Gln Tyr Ala Pro Gly Tyr His Phe Leu
        195                 200                 205

Leu Ser Ile Ala Ala Pro Ala Gly Pro Glu His Tyr Ser Phe Leu His
210                 215                 220

Met Ser Asp Leu Gly Gln Val Leu Asp Tyr Val Asn Leu Met Ala Tyr
225                 230                 235                 240

Asp Tyr Ala Gly Ser Trp Ser Tyr Ser Gly His Asp Ala Asn Leu
                245                 250                 255

Phe Ala Asn Pro Ser Asn Pro Asn Ser Ser Pro Tyr Asn Thr Asp Gln
            260                 265                 270

Ala Ile Lys Asp Tyr Ile Lys Gly Gly Val Pro Ala Ser Lys Ile Val
        275                 280                 285

Leu Gly Met Pro Ile Tyr Gly Arg Ala Phe Glu Ser Thr Gly Gly Ile
290                 295                 300

Gly Gln Thr Tyr Ser Gly Ile Gly Ser Gly Ser Trp Glu Asn Gly Ile
305                 310                 315                 320

Trp Asp Tyr Lys Val Leu Pro Lys Ala Gly Ala Thr Val Gln Tyr Asp
                325                 330                 335

Ser Val Ala Gln Ala Tyr Tyr Ser Tyr Asp Pro Ser Ser Lys Glu Leu
            340                 345                 350

Ile Ser Phe Asp Thr Pro Asp Met Ile Asn Thr Lys Val Ser Tyr Leu
        355                 360                 365

Lys Asn Leu Gly Leu Gly Gly Ser Met Phe Trp Glu Ala Ser Ala Asp
370                 375                 380

Lys Thr Gly Ser Asp Ser Leu Ile Gly Thr Ser His Arg Ala Leu Gly
385                 390                 395                 400

Ser Leu Asp Ser Thr Gln Asn Leu Leu Ser Tyr Pro Asn Ser Gln Tyr
                405                 410                 415

Asp Asn Ile Arg Ser Gly Leu Asn
            420

<210> SEQ ID NO 13
<211> LENGTH: 781
<212> TYPE: DNA
<213> ORGANISM: Alfalfa mosaic virus

<400> SEQUENCE: 13
atggtggagc acgacactct cgtctactcc aagaatatca agatacagt ctcagaagac        60 caaagggcta ttgagacttt tcaacaaagg gtaatatcgg gaaacctcct cggattccat       120
tgcccagcta tctgtcactt catcaaaagg acagtagaaa aggaaggtgg cacctacaaa       180
tgccatcatt gcgataaagg aaaggctatc gttcaagatg cctctgccga cagtggtccc       240
aaagatggac ccccacccac gaggagcatc gtggaaaaag aagacgttcc aaccacgtct       300
tcaaagcaag tggattgatg tgataacatg gtggagcacg acactctcgt ctactccaag       360
```

-continued

```
aatatcaaag atacagtctc agaagaccaa agggctattg agacttttca acaaagggta       420
atatcgggaa acctcctcgg attccattgc ccagctatct gtcacttcat caaaaggaca       480
gtagaaaagg aaggtggcac ctacaaatgc catcattgcg ataaaggaaa ggctatcgtt       540
caagatgcct ctgccgacag tggtcccaaa gatggacccc cacccacgag gagcatcgtg       600
gaaaaagaag acgttccaac cacgtcttca aagcaagtgg attgatgtga tatctccact       660
gacgtaaggg atgacgcaca atcccactat ccttcgcaag accttcctct atataaggaa       720
gttcatttca tttggagagg acacgctgaa atcaccagtc tctctctaca aatctatctc       780
t                                                                        781
```

TRANSGENIC DISEASE RESISTANT BANANA

RELATED APPLICATIONS

This is a continuation-in-part of PCT Patent Application No. PCT/IL2004/001032 having International Filing Date of Nov. 11, 2004, which claims the benefit of U.S. Provisional Patent Application No. 60/574,235, filed on May 26, 2004, and U.S. Provisional Patent Application No. 60/519,654, filed on Nov. 14, 2003. The contents of the above applications are all incorporated by reference.

FIELD AND BACKGROUND OF THE INVENTION

The present invention relates to genetically engineering banana plants and, more particularly, to introducing exogenous disease resistance traits to banana plants.

The global banana production exceeds 80 million tones annually and serves as an essential food item to about 400 million people residing in tropical and subtropical developing countries. In addition, banana produce is exported at a gross value exceeding 3 billion US$ annually thus providing a most necessary income of foreign currency to many developing countries.

The banana production is presently threatened by devastating diseases caused by pathogenic fungi, particularly the black leaf streak disease (BLSD) caused by *Mycosphaerella fijiensis* Morelet and the Sigatoka disease (SD) caused by *M. musicola* Leach ex Mulder. These pathogens attack all types of banana and are widespread in most banana producing regions where yield losses due to BLSD and SD may reach up to 30-50%.

Banana diseases caused by pathogenic fungi, such as BLSD and SD may be treated by fungicides, however effective fungicides are often too costly for use in developed countries. Furthermore, the presence of fungicide residue in exported fruit is increasingly restricted, due to health and environmental concerns, thus further limiting the practice of chemical control. Banana disease control by way of sanitation has been proven ineffective since it requires disciplined use of pathogen-free germplasm which is often lacking among growers in developing countries and since pathogens are capable of spreading via wind-borne spores.

A preferred approach for effectively controlling banana diseases, such as BLSD and SD, is by generating disease resistant banana cultivars. Traditional breeding of banana plants has produced BLSD-resistant diploid banana cultivars [e.g., "Paka" (AA) and "Pisang lilin" (AA)] however, disease-resistant triploid cultivars, such as "Cavendish" type dessert banana, have not been developed (Mourichon et al. 1997). Since traditional breeding of banana is hampered by long generation time (almost two years), large areas for field testing (6 m² per plant), triploidy and sterility of most edible cultivars, the use of genetic engineering techniques for conferring disease resistance to banana plants is highly desired (Sagi et al., 1995).

One approach of transforming banana plants involves the use of *Agrobacterium*-mediated delivery of exogenous DNA. For example, U.S. Pat. No. 6,133,035 describes a method of transforming banana through incubation with *Agrobacterium* cells carrying exogenous DNA including selectable marker genes nptII or ALS and a GUS reporter gene.

Another approach of transforming banana plants involves bombardment of embryogenic cells with accelerated microparticles carrying exogenous polynucleotides (microprojectiles). For example, Dugdale et al. (Journal of General Virology 79:2301-2311, 1998) describe transformation of embryogenic suspended cells of banana cv. "Bluggoe" (*Musa*, ABB group) by using microprojectiles bombardment. The microprojectiles used in transformation carried exogenous DNA including selectable marker genes, reporter genes (e.g., GUS or green fluorescent protein encoding sequence) and the banana bushy top virus DNA-6 promoter. The reporter genes were stably integrated in banana cells genomes and expressed in plants regenerated therefrom.

Yet, the prior art fails to describe successful generation of banana plants having disease resistance traits.

While reducing the present invention to practice, the present inventors successfully produced banana plants which carry and express exogenous polynucleotides encoding disease resistance traits.

SUMMARY OF THE INVENTION

According to one aspect of the present invention there is provided a nucleic acid construct or construct system which includes (i) a first polynucleotide encoding endochitinase, (ii) a second polynucleotide encoding stilbene synthase and (iii) a third polynucleotide encoding superoxide dismutase.

According to yet another aspect of the present invention there is provided a banana cell which includes a nucleic acid construct encoding at least one exogenous polypeptide capable of conferring disease resistance to the banana cell.

According to still another aspect of the present invention there is provided a banana plant which includes a nucleic acid construct encoding at least one exogenous polypeptide capable of conferring disease resistance to the banana plant.

According to an additional aspect of the present invention there is provided a method of producing a disease resistant banana plant which includes transforming a banana cell with a nucleic acid construct encoding at least one exogenous polypeptide capable of conferring disease resistance to the banana cell and regenerating a banana plant from the banana cell, thereby producing the disease resistant banana plant.

According to further features in preferred embodiments of the invention described below, the nucleic acid construct further includes at least one promoter capable of directing transcription of the first polynucleotide the second polynucleotide and the third polynucleotide in plant cells.

According to still further features in the described preferred embodiments the nucleic acid construct further includes an internal ribosome entry site sequence.

According to still further features in the described preferred embodiments the polynucleotide encoding endochitinase is set forth in SEQ ID NO: 1.

According to still further features in the described preferred embodiments the polynucleotide encoding stilbene synthase is set forth in SEQ ID NO: 2.

According to still further features in the described preferred embodiments the polynucleotide encoding superoxide dismutase is set forth in SEQ ID NO: 3.

According to still further features in the described preferred embodiments the at least one exogenous polypeptide is selected from the group consisting of an endochitinase, a stilbene synthase and a superoxide dismutase.

According to still further features in the described preferred embodiments the stilbene synthase is set forth in SEQ ID NO: 10.

According to still further features in the described preferred embodiments the superoxide dismutase is set forth SEQ ID NO: 11.

According to still further features in the described preferred embodiments the endochitinase is set forth in SEQ ID NO: 12.

According to still further features in the described preferred embodiments the banana cell is an embryogenic banana cell.

According to still further features in the described preferred embodiments the embryogenic banana cell is included in a callus.

According to still further features in the described preferred embodiments the transforming is effected by microprojectiles bombardment.

According to still further features in the described preferred embodiments the regenerating is effected by micropropagation.

The present invention successfully addresses the shortcomings of the presently known configurations by providing nucleic acid constructs including one or more polynucleotides encoding disease resistance polypeptides, transformed banana cells and transformed banana plants expressing exogenous disease resistance traits, and methods of producing same.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 illustrates the germination incidence of *Botrytis cinerea* spores following four hours incubation in solutions containing leaf extract obtained from wild-type and transformed banana plants.

FIGS. 2A-B are PCR analyses illustrating the presence of nptII gene (FIG. 2A) and STS gene (FIG. 2B) in transformed banana plants. Lanes 1-9: different transformed plants; lane 10: plasmid pYC39 (positive control); lane 11: a wild-type control; and lane 12: λEcoRI+HindIII size markers.

Figure 1:
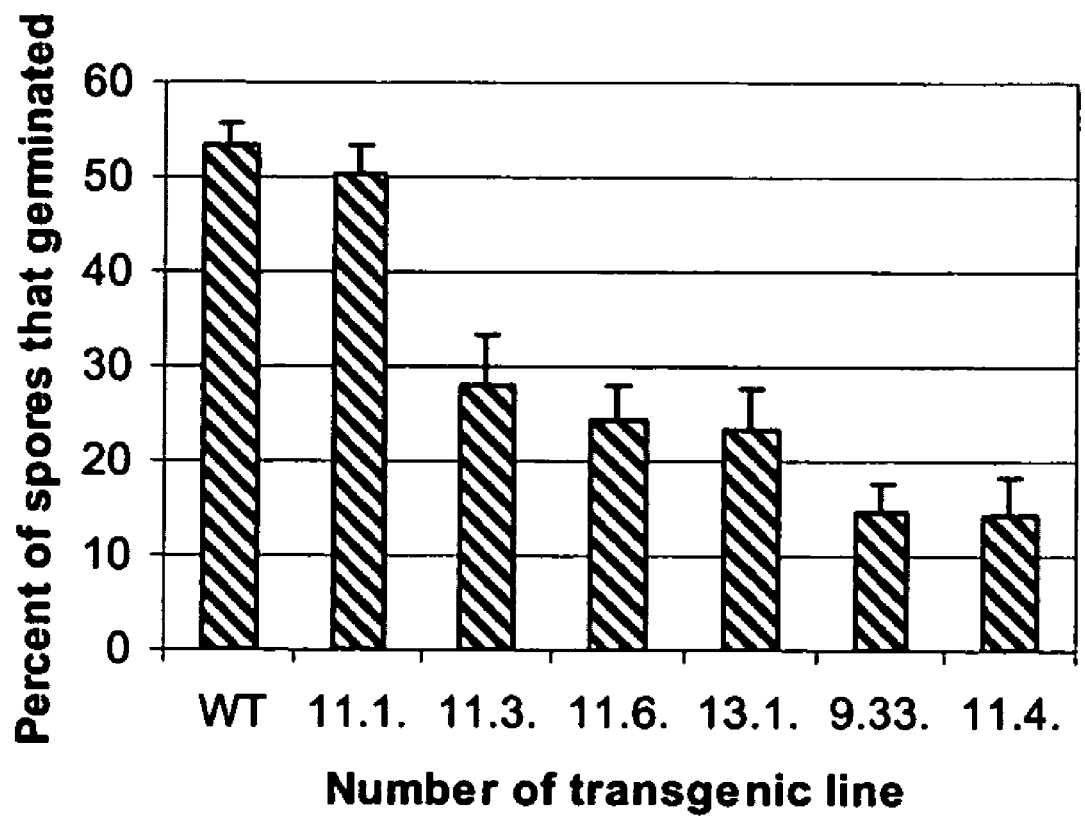
Figure 3:
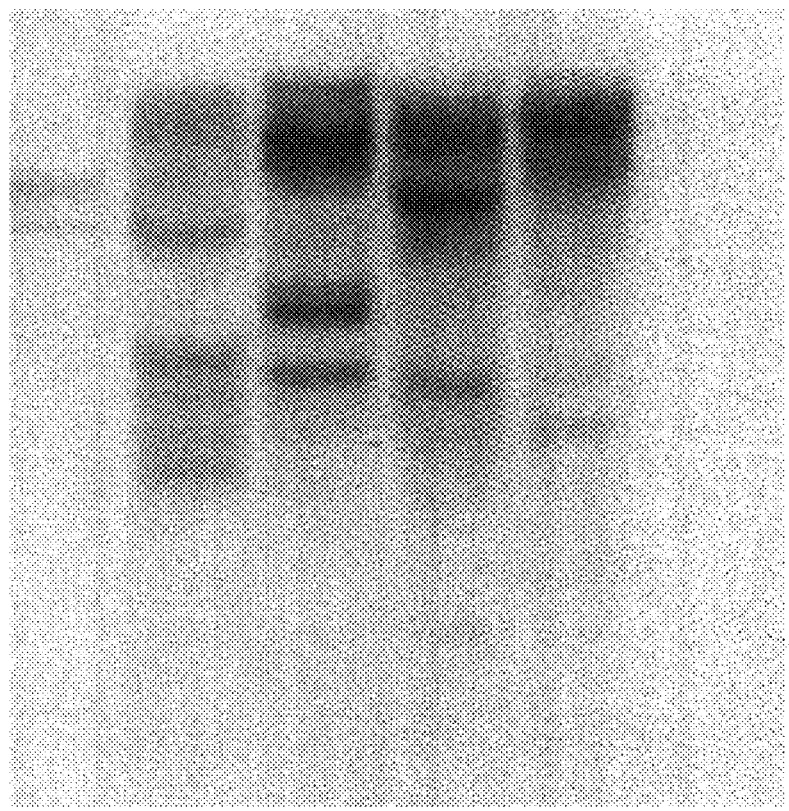

FIG. 3 illustrates a Southern blot analysis of genomic DNA digested with HindIII and probed with nptII. Lanes 1-5: different transformed banana plants; lane 6: wild-type control.

Figure 4:
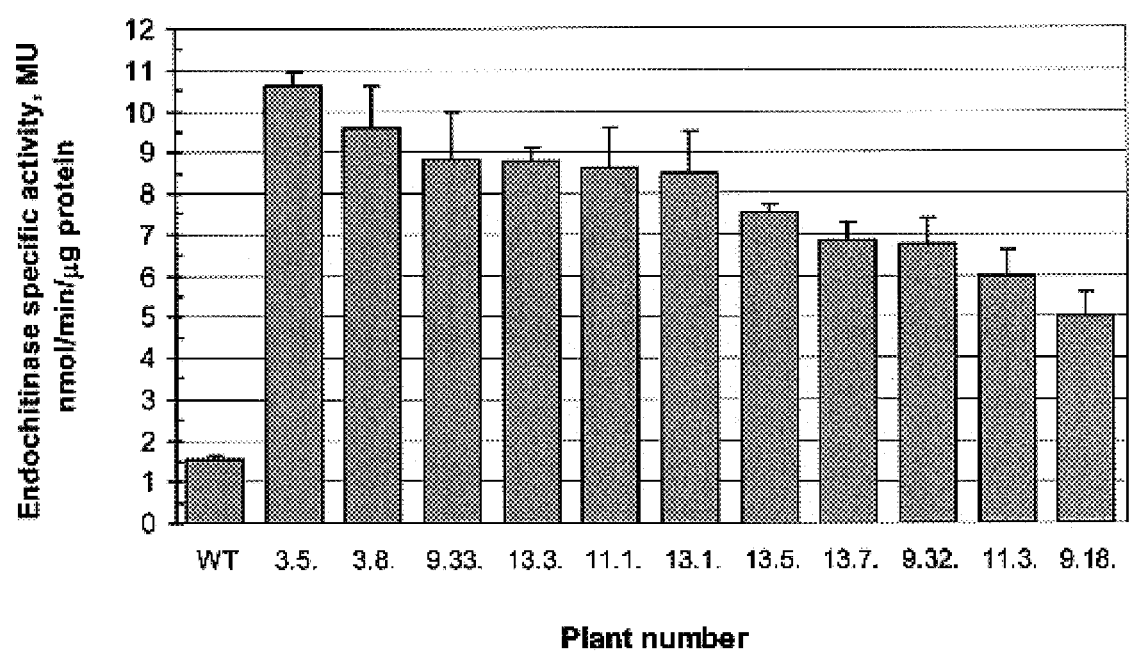

FIG. 4 illustrates endochitinase activity in leaves of transformed banana plants.

Figure 5:
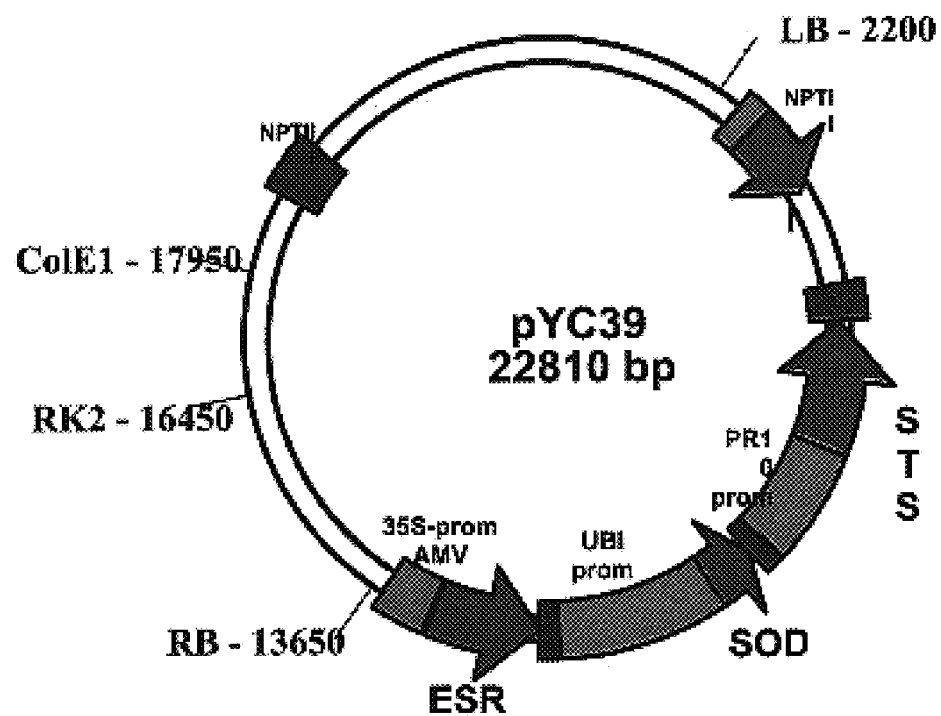

FIG. 5 is a plasmid map illustrating the nucleic acid construct pYC39. The pYC39 construct includes an endochitinase gene (ESR), flanked by the 35S-35S-AMV promoter and NOS terminator; the superoxide dismutase gene (SOD), flanked by the Ubi 1 promoter and NOS terminator; and the stilbene synthase gene (STS) flanked by the PR10 promoter and 35S PA terminator.

Figure 6:
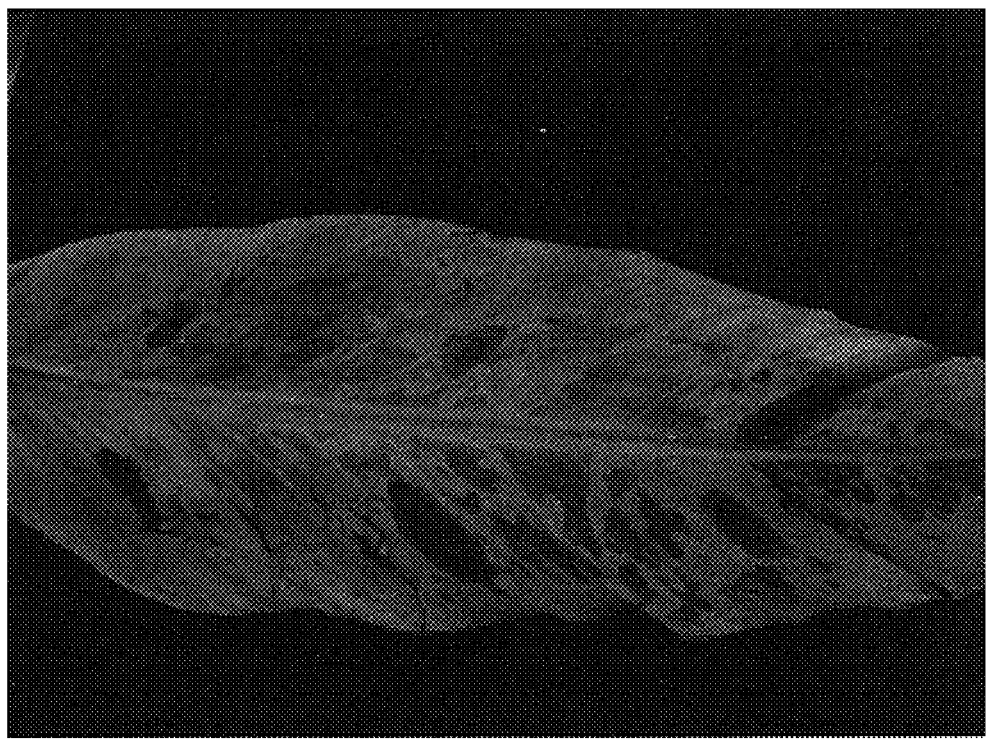

FIG. 6 is a photograph illustrating a leaf of wild type (non-transgenic) banana plant which was inoculated with *Botrytis cinerea* and exhibits necrotic leaf spots.

Figure 7:

FIG. 7 is a photograph illustrating a leaf of a transgenic banana plant which was inoculated with *Botrytis cinerea* but does not exhibit necrotic leaf spots.

Figure 8A:
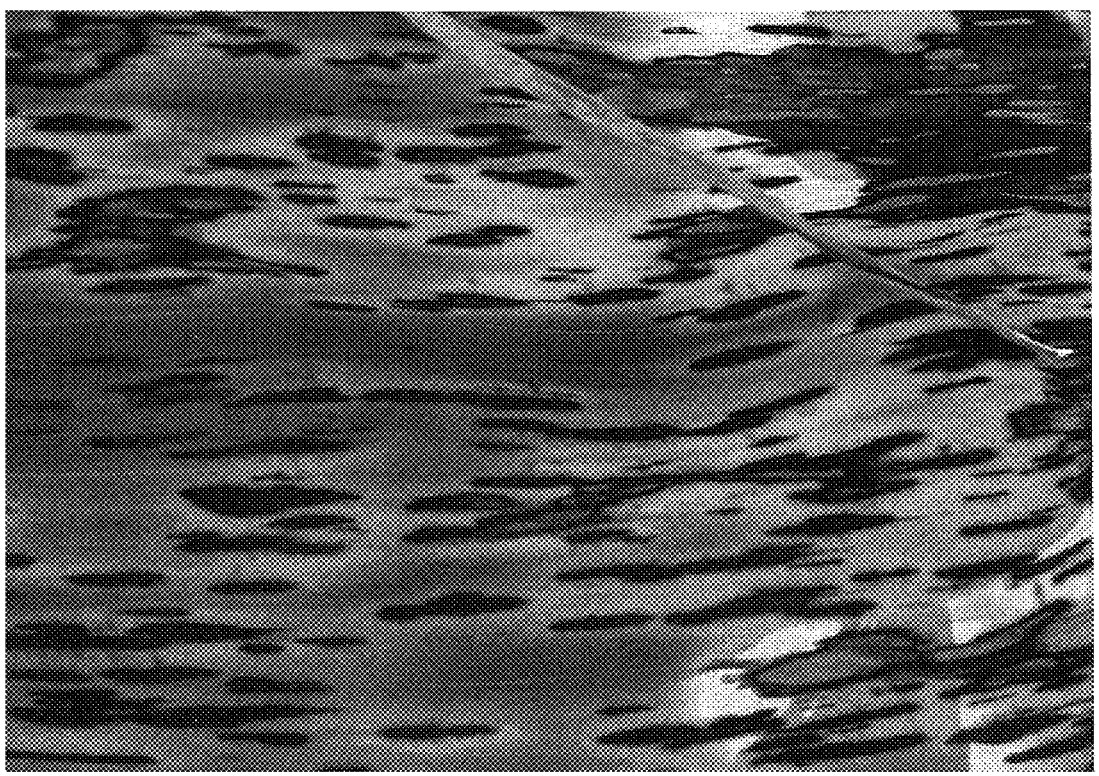
Figure 8B:
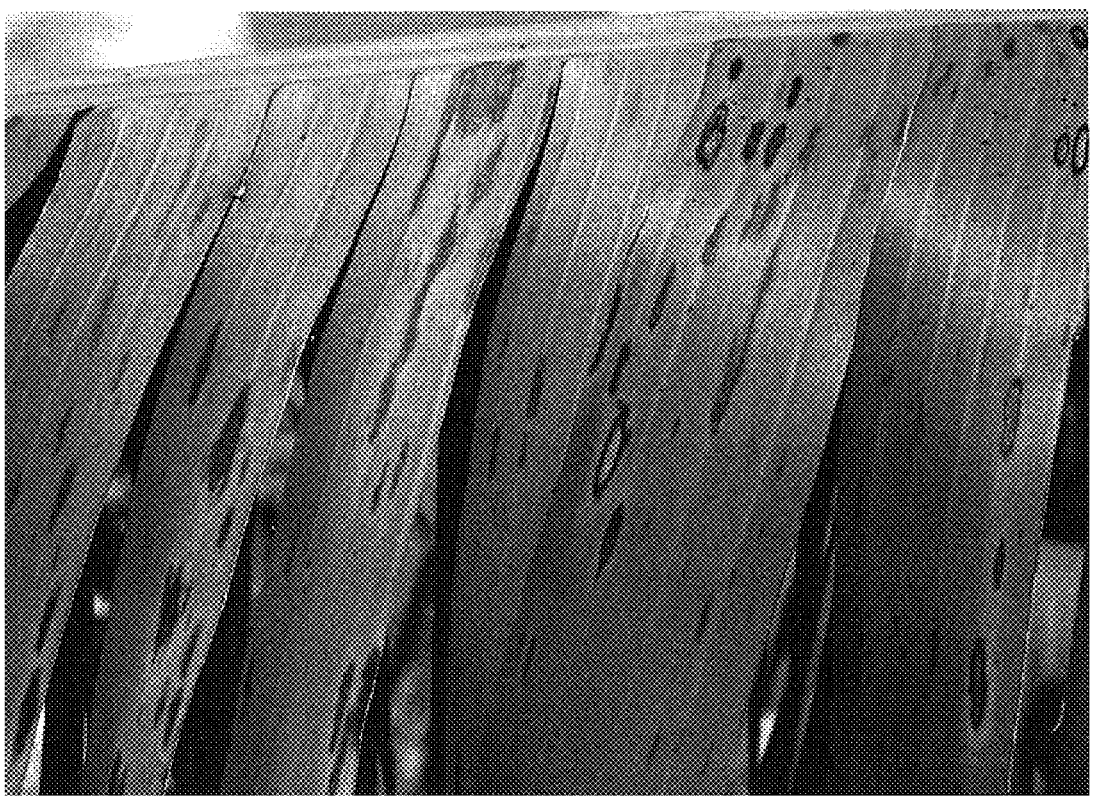
Figure 8C:
Figure 8D:

FIGS. 8a-d are photographs showing the severity of the sigatoka symptoms in control non transgenic banana i.e., Grand Nain banana plants (FIG. 8a) as well as in various transgenic plants expressing two (FIG. 8d) or three (FIG. 8b) exogenous polypeptides conferring disease resistance. Of note, a transgenic plant which expressed no detectable level of the transgenes (FIG. 8c) was susceptible to *Mycosphaerella* spp. infection as the control non-trangenic plant. However, a transgenic plant which expressed all three transgenes was resistant to the infection (FIG. 8b).

DESCRIPTION OF THE PREFERRED EMBODIMENTS

The present invention is of nucleic acid constructs and plants transformed with the nucleic acid constructs and methods of producing same. Specifically, the present invention is of transforming banana plants with exogenous polynucleotides encoding disease resistance traits.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As mentioned hereinabove, techniques for transforming and regenerating banana plants are known in the art (see, for example, U.S. Pat. No. 6,133,035; Sagi et al., Bio/Technology 13, 481-485, 1995; May et al., Bio/Technology 13, 485-492, 1995; Zhong et al., Plant Physiol. 110, 1097-1107, 1996; and Dugdale et al., Journal of General Virology 79:2301-2311, 1998). However, the prior art fails to describe transgenic banana plant exhibiting disease resistance traits.

While reducing the present invention to practice and as is described hereinabove, the present inventors constructed an expression construct (pYC39) which includes polynucleotide sequences encoding endochitinase, superoxide dismutase and stilbene synthase (Example 3). The pYC39 construct of the present invention was successfully introduced into embryogenic callus of commercial banana (Example 4) and the resulting transformed cells were successfully regenerated into plants (Example 2). The transgenic banana plants produced by the present inventors exhibited endochitinase expression and pathogen resistance (Example 5).

Thus, according to one aspect of the present invention, there is provided a method of producing a disease resistant banana plant. The method is effected by transforming a banana cell with at least one exogenous polynucleotide encoding a polypeptide capable of conferring disease resistance to a banana plant.

The banana cell of the present invention can be any banana variety or cultivar, including, but not limited to, *Musa* sp. AAA group cv. 'Grand Nain'. Preferably, the banana cell used for transformation is an embryogenic cell which is capable of forming a whole plant. More preferably, the banana cell is an embryogenic callus cell.

The phrase "embryogenic callus cell" used herein refers to an embryogenic cell contained in a cell mass produced in vitro.

Banana embryogenic callus cells suitable for transformation can be generated using well known methodology. For example, immature male flowers (influorescences) can be dissected and incubated in M1 medium (see content in Table 1 hereinbelow) under a reduced light intensity (50-100 lux) at 25° C. Following 3-5 months of incubation in M1 medium, yellow embryogenic calli are transferred to M2 medium (see content in Table 1 below) and incubated at 27° C. in the dark for at least four months to promote embryogenesis.

As is mentioned hereinabove, such banana embryogenic callus cells are suitable for transformation with a nucleic acid construct which includes at least one polynucleotide encoding a disease resistance polypeptide.

The phrases "polypeptide capable of conferring disease resistance" and "disease resistance polypeptide" are interchangeably used herein to refer to any peptide, polypeptide or protein which is capable of protecting a banana plant (expressing the polypeptide) from pathogen infection or the harmful effects resultant from pathogen infection.

Such a polypeptide can be an antimicrobial enzyme such as, for example, a chitinase (see, for example, in U.S. Pat. Nos. 4,940,840, 5,173,419; and by Collinge et al., Plant Journal, 3:31-40, 1993), a glucanase (see, for example, in U.S. Pat. Nos. 6,563,020, 5,530,187 and 5,168,064; and in Christoffersen et al, Plant Molec. Biol., 3:385, 1984; Tucker et al., Plant Physiol., 88:1257, 1988; Payne et al., Plant Mol. Biol., 15:797-808, 1990; Ward et al., Plant Physiol., 96:390-397, 1991; and Linthorst et al., PNAS,USA, 87:8756-8760, 1990), or other antimicrobial lytic enzymes such as described by Boller T. ("Hydrolytic enzymes in plant disease resistance." in T. Kosuge, E. W. Nester, eds. Plant-Microbe Interactions. Vol 2: 385-413, 1987).

Alternatively, or additionally, a suitable disease resistance polypeptide can be a pathogenesis-related (PR) protein such as described, for example, in U.S. Pat. Nos. 6,479,731, 6,653, 533, 6,646,183, 6,287,865, 5,648,599, 5,859,351 and 5,859, 339; and by Bol et al.,(Ann. Rev. Phytopathol., 28:113-138, 1990), Bohlmann et al., (EMBO J., 7:1559-1565, 1988), Vigers et al. (Mol. Plant Micro. Interactions, 4:315-323, 1991), Leach et al. (J. Biol. Chem., 266:1564-1573, 1990), Moreno et al. (PNAS, USA, 86:7885-7889, 1989), Garcia-Olmedoz et al. (Surv. Plant Mol. Cell Biol., 4:275-334, 1987), Johal et al., (Science 258:985-987, 1992), Martinet et al., (Science 262:1432-1436, 1993), Jones and Jones (Adv. Bot. Res. Incorp. Adv. Plant Pathol. 24:89-167, 1997), Song et al. (Science 270:1804-1806, 1995), Bent et al. (Science 265: 1856-1860, 1994), Mindrinos et al. (Cell 78:1089-1099, 1994) and Grant et al., 1995, Science 269:843-846, 1995).

A suitable disease resistance polypeptide can also be a polypeptide capable of inducing or enhancing resistance in plants such as described, for example in U.S. Pat. Nos. 6,091, 004 and 6,316,697.

As is mentioned hereinabove, the method of the present invention is effected by transforming a banana cell with at least one polynucleotide encoding a poly eptide capable of conferring disease resistance to a banana plant.

Preferably, the banana cell is transformed with a polynucleotide sequence encoding endochitinase, an example of which is set forth in SEQ ID NO: 1.

Since plants transformed with just a single exogenous disease-resistance polypeptide, such as endochitinase, typically exhibit only partial and short-lasting protection (see, for example, in Jach et al., Plant J. 8:97-108, 1995) the banana cell/plant of the present invention preferably expresses a plurality of exogenous disease resistance polypeptides and is thus substantially more disease resistant than prior art plants.

Thus, the banana cell is also transformed with a polynucleotide sequence encoding stilbene synthase. An example of such a polynucleotide sequence is set forth by SEQ ID NO: 2.

Preferably, the banana cell is also transformed with a polynucleotide sequence encoding superoxide dismutase. An example of such a polynucleotide sequence is set forth by SEQ ID NO: 3.

Several approaches can be utilized to transform and co-express these polynucleotides in plant cells.

Although less preferred, each of the above described polynucleotide sequences can be separately introduced into a banana cell by using three separate nucleic-acid constructs.

Preferably, the three polynucleotide sequences can be co-introduced and co-expressed in the banana cell using a single nucleic acid construct.

Such a construct can be designed with a single promoter sequences co-which can transcribe a polycistronic message including all three polynucleotide sequences.

To enable co-translation of the three polypeptides encoded by the polycistronic message, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the three polypeptides described above will be translated from both the capped 5' end and the two internal IRES sequences of the polycistronic RNA molecule to thereby produce in the cell all three polypeptides.

Alternatively, the polynucleotide segments encoding the plurality of polypeptides capable of conferring disease resistance can be translationally fused via a protease recognition site cleavable by a protease expressed by the cell to be transformed with the nucleic acid construct. In this case, a chimeric polypeptide translated will be cleaved by a cell-expressed protease to thereby generate the plurality of polypeptides.

Preferably, the present invention utilizes a nucleic acid construct which includes three promoter sequences each capable of directing transcription of a specific polynucleotide sequence of the polynucleotide sequences described above.

Suitable promoters which can be used with the nucleic acid of the present invention include constitutive, inducible, or tissue-specific promoters.

Suitable constitutive promoters include, for example, CaMV 35S promoter (Odell et al., Nature 313:810-812, 1985); maize Ubi 1 (Christensen et al., Plant Sol. Biol. 18:675-689, 1992); rice actin (McElroy et al., Plant Cell 2:163-171, 1990); pEMU (Last et al., Theor. Appl. Genet. 81:581-588, 1991); and Synthetic Super MAS (Ni et al., The Plant Journal 7: 661-76, 1995). Other constitutive promoters include those in U.S. Pat. Nos. 5,659,026, 5,608,149; 5,608, 144; 5,604,121; 5,569,597: 5,466,785; 5,399,680; 5,268,463; and 5,608,142.

Suitable inducible promoters can be pathogen-inducible promoters such as, for example, the alfalfa PR10 promoter (Coutos-Thevenot et al., Journal of Experimental Botany 52: 901-910, 2001 and the promoters described by Marineau et al., Plant Mol. Biol. 9:335-342, 1987; Matton et al. Molecular Plant-Microbe Interactions 2:325-331, 1989; Somsisch et al., Proc. Natl. Acad. Sci. USA 83:2427-2430, 1986: Somsisch et al., Mol. Gen. Genet. 2:93-98, 1988; and Yang, Proc. Natl. Acad. Sci. USA 93:14972-14977, 1996.

Suitable tissue-specific promoters include, but not limited to, leaf-specific promoters such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993.

Preferably, the nucleic acid construct of the present invention includes the promoter set forth in SEQ ID NO: 13 operably linked to the polynucleotide set forth in SEQ ID NO: 1; the promoter set forth in SEQ ID NOs: 4 operably linked to the polynucleotide set forth in SEQ ID NO: 2; and the promoter set forth in SEQ ID NOs: 5 operably linked to the polynucleotide set forth in SEQ ID NO: 3.

The nucleic acid construct of the present invention may also include at least one selectable marker such as, for example, nptII. Preferably, the nucleic acid construct is a shuttle vector, which can propagate both in *E. coli* (wherein the construct comprises an appropriate selectable marker and origin of replication) and be compatible for propagation in cells. The construct according to the present invention can be, for example, a plasmid, a bacmid, a phagemid, a cosmid, a phage, a virus or an artificial chromosome, preferably a plasmid.

The nucleic acid construct of the present invention can be utilized to stably transform banana cells. The principle methods of causing stable integration of exogenous DNA into banana genome include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. Suitable *Agrobacterium*-mediated procedures for introducing exogenous DNA to banana cells is described by Dougale et al. (Journal of General Virology, 79:2301-2311, 1998) and in U.S. Pat. No. 6,395,962.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Alternatively, the nucleic acid construct of the present invention can be introduced into banana cells by a microprojectiles bombardment. In this technique, tungsten or gold particles coated with exogenous DNA are accelerated toward the target cells. Suitable banana transformation procedures by microprojectiles bombardment are described by Sagi et al. (Biotechnology 13:481-485, 1995) and by Dougale et al. (Journal of General Virology, 79:2301-2311, 1998). Preferably, the nucleic acid construct of the present invention is introduced into banana cells by a microprojectiles bombardment procedure as described in Example 4 hereinbelow.

Following transformation, the transformed cells are micropropagated to provide a rapid, consistent reproduction of the transformed material.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Thus, transformed banana cells can be micropropagated and regenerated into plants using methods known in the art such as described, for example in U.S. Pat. No. 6,133,035 and by Novak et al., 1989; Dhed'a et al., 1991; Cote et al., 1996; Becker et al., 2000; Sagi et al. Plant Cell Reports 13:262-266, 1994; Grapin et al., Cell Dev. Biol. Plant. 32:66-71, 1996; Marroquin et al., In Vivo Cell. Div. Biol. 29P:43-46, 1993; and Escalant et al., In Vivo Cell Dev. Biol. 30:181-186, 1994).

Preferably, transformed banana cells are selected for antibiotic resistance and regenerated into planlets using the procedure described in Example 4 in the Examples section which follows. Briefly, several days following transformation treatment (e.g., microprojectiles bombardment), treated banana embryogenic calli which include transformed cells, are transferred to a selection medium supplemented with a selection agent, such as liquid selection medium is M2 containing 75 mg/1 Par (15 ml medium in 100 ml flask). Following two weeks incubation in the dark, the calli are transferred to liquid M2 medium (see content in Table 1 hereinbelow) supplemented with 100 mg/1 Par (25 ml medium in 100 ml flask) for additional two weeks incubation in the dark, then transferred to liquid M3 medium (Table 2) supplemented with 100 mg/1 Par (25 ml medium in 100 ml flask) for additional 1-2 weeks incubation in the dark. Following incubation in liquid selection media, the calli are transferred to a regeneration semi-solid medium, such as E1 medium (Table 2) supplemented with 150 mg/1 Par. The calli are incubated in the regeneration medium for three months in the dark, with sub-culturing to fresh media every 4-6 weeks. Following incubation, aggregates with mature embryos and secondary embryos are transferred to R1 semi-solid medium supplemented with 200 mg/1 Par for two months incubation, then transferred to R2 semi-solid medium (Table 3) supplemented with 200 mg/1 Par for additional three months incubation. Following incubation, germinated embryos are rooted in P1 semi-solid medium (Table 3) supplemented with 200 mg/1 Par in Magenta boxes (Sigma). Subsequently, the transformed plantlets are transferred to a greenhouse for hardening.

Stable integration of exogenous DNA sequence in the genome of the transformed plants can be determined using standard molecular biology techniques well known in the art such as PCR and Southern blot hybridization (see, for example, in Example 5 hereinbelow).

Although stable transformation is presently preferred, transient transformation of cultured cells, leaf cells, meristematic cells or the whole plant is also envisaged by the present invention.

Transient transformation can be effected by any of the direct DNA transfer methods described above or by viral infection using modified plant viruses.

Viral infection is preferred since is enables circumventing micropropagation and regeneration of a whole plant from cultured cells. Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman et al. (Communications in Molecular Biology: Viral Vectors, Cold Spring Harbor Laboratory, New York, pp. 172-189, 1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson et al. (Virology 172:285-292, 1989; Takamatsu et al. EMBO J. 6:307-311, 1987; French et al. (Science 231:1294-1297, 1986); and Takamatsu et al. (FEBS Letters 269:73-76, 1990).

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA.

If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that the sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

In addition to the above, the nucleic acid molecule of the present invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenbus nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Expression of exogenous polypeptides in transformed plants can be determined using standard molecular biology techniques well known in the art such as, for example, Northern blot analysis and Western blot analysis. Alternatively, expression of exogenous polypeptides can be determined based on specific phenotypic traits.

In case that the exogenous polypeptide is an enzyme, the expression can be determined based on the enzyme specific activity. For example, exogenous endochitinase activity in transformed plant tissue can be measured, in comparison with similar wild-type (non-transformed) plant tissue, using methods such as described in Example 5 hereinbelow. A substantial increase in endochitinase activity in transformed plant tissue would indicate expression of exogenous endochitinase.

In case that the exogenous polypeptide confers disease resistance to the plant, the expression can be determined based on increased in resistance or tolerance to pathogens, preferably in comparison with similar wild-type (non-transformed) plant. Comparative evaluation of plants for their resistance or tolerance to pathogens can be effected using in vitro or in vivo bioassays well known in the art of plant pathology such as described, for example by Agrios, G. N., ed. (Plant Pathology, Third Edition, Academic Press, New York, 1988).

Evaluating plant resistance or tolerance to pathogens can be effected by exposing a pathogen to an extract obtained from plant tissue and determining the effect of the extract on the pathogen growth in vitro, using a procedure such as described in details in Examples 5-6 hereinbelow. Preferably, evaluating plant resistance or tolerance to pathogens pathogens is effected by exposing a pathogen to a plant tissue (e.g., a leaf tissue) such as described in details in Examples 7 hereinbelow. More preferably, evaluating plant resistance or tolerance to pathogens is effected by exposing a pathogen to a whole plant. For example, evaluating plant resistance or tolerance to *Mycosphaerella musicola* (the causal agent of black Sigatoka disease) can be effected by planting transformed banana plants in an open field in a close proximity to non-transformed plants which are infected with the pathogen (used as a source of inoculum). The disease severity which subsequently develops in transformed plants is evaluated comparatively to non-transformed plants. The disease severity is preferably evaluated visually (the damage usually appears on suckers which have at least 10-12 leaves) and statistically analyzed to determine significant differences in resistance or tolerance between plant lines to the black Sigatoka disease.

Hence, the present invention provides nucleic acid constructs including one or more polynucleotides encoding disease resistance polypeptides, transformed banana cells and transformed banana plants expressing exogenous disease resistance traits, and methods of producing same.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons; Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984);

"Animal Cell Culture" Freshney, R. I., ed. (1986); "Immobilized Cells and Enzymes" IRL Press, (1986); "A Practical Guide to Molecular Cloning" Perbal, B., (1984); "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996) and Parfitt et al. (1987). Bone histomorphometry: standardization of nomenclature, symbols, and units. Report of the ASBMR Histomorphometry Nomenclature Committee. J. Bone Miner Res 2 (6), 595-610; all of which are incorporated by reference as if fully set forth herein. Other general references are provided throughout this document. The procedures therein are believed to be well known in the art and are provided for the convenience of the reader. All the information contained therein is incorporated herein by reference.

Example 1

Initiation and Propagation of Banana Embryogenic Callus

Immature male flowers of banana (*Musa* AAA cv. 'Grand Nain') were surface sterilized with 10% sodium hypochlorite for 30 minutes, dissected and incubated in M1 medium (see content in Table 1 below) under a reduced light intensity (50-100 lux) at 25° C. Following 3-5 months of incubation in M1 medium, yellow embryogenic calli were transferred to M2 medium (see content in Table 1 below) and incubated at 27° C. in the dark for at least four months to promote embryogenesis.

TABLE 1

Media for initiation and maintenance of embryogenic calli

| Ingredients | M1 | M2 |
| --- | --- | --- |
| Salt mixture | MS | MS |
| Vitamin mixture | MS | MS |
| Biotin, mg $l^{-1}$ | 1 | 1 |
| Sucrose, g $l^{-1}$ | 30-45 | 44.5 |
| NAA mg $l^{-1}$ | 1 | |
| 2,4-D, mg $l^{-1}$ | 4 | 1 |
| IAA mg $l^{-1}$ | 1 | |
| Glutamine, mg $l^{-1}$ | | 100 |
| Malt extract, mg $l^{-1}$ | | 100 |
| DTT, mg $l^{-1}$ | 50 | |
| Agarose, g $l^{-1}$ | 7 | |
| Gelrite (Duchefa), g $l^{-1}$ | 2.5 | 2 |
| pH | 5.7 | 5.3 |

MS = According to Murashig and Skoog, 1962)
NAA = α-naphthalane acetic acid
IAA = Indole aetic acid
DTT = 2,4-dichlorophenoxy acetic acid (2,4 D)

Example 2

Regeneration of Banana Plants from Embryogenic Calli

Embryogenic calli were incubated in E1 or E3 medium (see content in Table 2 below) at 27° C. in the dark for 2-3 months and then transferred to M3 medium for additional incubation under similar conditions. During incubation, abundant primary and secondary embryos (i.e., somatic embryos which developed from pre-existing embryos) were formed.

TABLE 2

Media for induction of banana embryos

| Ingredients | E1 | E3 | M3 | M3a |
| --- | --- | --- | --- | --- |
| Mineral salts | SH | SH | SH | MS |
| Vitamins | MS | MS | MS | MW |
| Biotin, mg $l^{-1}$ | 1 | 1 | 1 | 1 |
| Glutamine, mg $l^{-1}$ | 100 | 100 | 100 | 100 |
| Malt extract, mg $l^{-1}$ | 100 | 100 | 100 | 100 |
| Proline, m $l^{-1}$ | 230.2 | 230.2 | 230.2 | 230.2 |
| Adenine sulfate, mg $l^{-1}$ | 10 | 1 | | |
| Maltose, g $l^{-1}$ | 15 | | | |
| Sucrose, g $l^{-1}$ | 45 | 45 | 45.5 | 44.5 |
| NAA, mg $l^{-1}$ | 0.2 | 0.2 | 0.2 | 0.2 |
| Kinetin, mg $l^{-1}$ | | | 0.1 | 0.1 |
| 2 iP, mg $l^{-1}$ | | 0.2 | 0.14 | 0.14 |
| BA, mg $l^{-1}$ | 0.2 | | | |
| Zeatin riboside, mg $l^{-1}$ | 0.05 | 0.05 | 0.05 | 0.05 |
| Gelrite, g $l^{-1}$ | 2.7 | 2.7 | 2.7 | 2.5 |
| pH | 5.3 | 5.3 | 5.3 | 5.3 |

SH = According to Schenk and Hildenbrandt (1972)
MS = According to Murashig and Skoog (1962)
MW = According to Morel and Wetmore.
NAA = α-naphthalane acetic acid
2 iP = 6-(γ,γ-Dimethylallylamino) purine
BA = 6-Benzylaminopurine Propagated embryos were transferred to R2 medium (see content in Table 3 below) and incubated under 16/8 light/dark conditions for 4-16 months with monthly transferring to fresh media to generate plantlets. Plantlets were rooted for 1-2 months in P1 or P2 medium, hardened in P3 medium for two months and propagated in BAM medium (see content of media in Table 3 below).

TABLE 3

Media for induction of banana plantlets

| Ingredients | R1 | R2 | P1 | P2 | P3 | BAM |
| --- | --- | --- | --- | --- | --- | --- |
| Mineral salts | MS | WP | MS | MS | MS | MS |
| Vitamins | MS | WP | MS | MS | MS | MS |
| Sucrose, g $l^{-1}$ | 30 | 30 | 30 | 30 | 30 | 30 |
| BA, mg $l^{-1}$ | 0.2 | 0.2 | | 0.2 | | |
| 2 iP, mg $l^{-1}$ | | | | | | 3 |
| NaH$_2$PO$_4$ × H$_2$O, mg $l^{-1}$ | | | | | | 398 |
| Adenine hemisulfate, mg $l^{-1}$ | | | | | | 160 |
| Zeatin riboside, mg $l^{-1}$ | 0.05 | 0.05 | | | | |
| AC, mg $l^{-1}$ | 0.5 | 0.5 | | 0.5 | 0.5 | 0.5 |
| Gelrite, g $l^{-1}$ | 2.5 | 2.5 | 2.5 | 2.5 | 2.5 | 2.5 |
| pH | 5.8 | 5.8 | 5.8 | 5.8 | 5.8 | 5.6 |

MS = According to Murashig and Skoog (1962)
WP = McCown's Woody Plant.
2 iP = 6-(γ,γ-Dimethylallylamino) purine
BA = 6-Benzylaminopurine
AC = Activated charcoal

Example 3

Construction of a Nucleic Acid Construct Comprising Genes Encoding the Enzymes Endochitinase, Superoxide Dismutase and Stilbene Synthase (Disease Resistant Traits)

Construction of pBluscript IISK-ESR: A polynucleotide fragment comprising the Trichoderma harzianum endochitinase gene ThEn-42 (ESR; SEQ ID NO: 1; Lorito et al., 1993). A fragment HindIII/EcoRI of pBIN19ESRI, carrying the duplicated 35S promoter, the AMV leader 5' to the ESR fragment and the NOS terminator was cloned into the HindIII/EcoRI sites of the plasmid pBluescript II SK (Stratagene)

under the control of the cauliflower mosaic virus 35S subunit promoter (CaMV-35S; Benfey et al. EMBO J. 9: 1685-1696, 1990) and the *Agrobacterium* nopaline synthase (NOS) terminator.

Construction of pBluescript IISK-ESR-SOD: A 840 bp polynucleotide fragment comprising cDNA of tomato superoxide dismutase gene (SOD; SEQ ID NO: 3; Perl et al., 1993) and NOS terminator was obtained as an EcoRI fragment of p492-P31A (Perl et al., 1993) and cloned in the EcoRI site of the pBluscript IISK-ESR construct. The Ubi 1 promoter of maize polyubiquitin gene (SEQ ID NO: 5; Christensen and Quail, 1996) was inserted in the BamHI site 5' to the SOD gene and the NOS terminator to generate pBluscript IISK-ESR-SOD-UBI.

Construction of pBINPLUS-STS: A polynucleotide fragment comprising the grape stilbene synthase gene cDNA (STS; Hain et al., 1993; Wiese et al., 1994; SEQ ID NO: 2) was obtained from total RNA of grape by reverse-transcriptase polymerase chain-reaction (RT-PCR) and the primers set forth in SEQ ID NOs: 8-9. The isolated STS gene was cloned in pGEM plasmid (Promega).

A polynucleotide fragment comprising the fungal-inducible promoter PR10 was isolated from genomic DNA of *Medicago sativa* using the PCR. The isolated PR10 promoter was fused with the 5' end of the STS gene and cloned in the EcoRI/SalI sites of the binary plasmid pBINPLUS (Engelen et al., 1995)

A polynucleotide fragment comprising the 35PA terminator (GeneBank Accession Number AF078810) was inserted downstream of the STS gene to form the pBINPLUS-STS construct.

Construction of pYC39: The KpnI/NotI fragment (filled by Klenow) of the pBluscript IISK-ESR-SOD-UBI-Prom construct described above was cloned into the EcoRI site (filled by Klenow) of pBINPLUS-STS (see plasmid map in FIG. 5).

Example 4

Transformation of Banana Plants with pYC39

Pre-bombardment preparation of embryogenic calli: Embryogenic calli generated as described in Example 1 above were cultured in 250 ml flasks containing 50 ml liquid M2 medium (see content in Table 1 hereinabove). The flasks were incubated for 3-6 week on a shaker (at 100 rpm) and kept in the dark. Following initial incubation, yellow calli clusters were sieved through a 1 mm mesh screen and cultured in a fresh liquid M2 medium for an additional period of 1-4 weeks. Following incubation in M2, the calli (0.7-1 gr) were arranged on a Whatman filter paper at a 25-30 mm diameter circle. The calli-containing filter paper. disks were placed on semi-solid M2 medium supplemented with Sorbitol (125 mM) and Mannitol (125 mM) and incubated for 4-6 hours prior to bombardment.

Preparation of pYC39-coated microprojectiles: The pYC39 plasmid, generated as described in Example 3 hereinabove, was purified using Qiagen plasmid purification Maxi Kit according to the manufacturer's instructions. Sixty milligrams gold particles (BIO-RAD; 1.0 µm i.d) were washed one time in 70% (v/v) ethanol and three times in sterile 50% (v/v) glycerol then suspended 0.5 ml of sterile 50% (v/v) glycerol. Coating of pYC39 on the gold particles was effected by mixing 50 µl of the gold particles suspension with 5 µg of plasmid pYC39, 50 µl of 2.5 M $CaCl_2$ and 20 µl of 0.1 M spermidine. The suspension of pYC39-coated gold particles was kept on crushed ice until used for bombardment Microprojectiles bombardment: Target calli tissues were placed 10 cm from the point of discharge of a particle inflow gun (BIO-RAD, Hercules, Calif.) and were bombarded twice with pYC39-coated gold particles delivered with a Helium pressure of 1350 PSI in a chamber having a vacuum pressure of 27 mm Hg.

Regeneration of bombarded plantlets: Following bombardment, the disks were placed on M2 medium supplemented with Sorbitol (63 mM) and Mannitol (63 mM) and incubated for 3-5 days at 27° C. in the dark. The bombarded calli were transferred from the filter paper disks to liquid M2 medium supplemented with 75 mg $l^{-1}$ paromomycin sulphate (Par) and incubated for 2 weeks. Following incubation, the calli were transferred to liquid M2 medium supplemented with 100 mg $l^{-1}$ Par for two weeks and thereafter to semi-solid E1 medium (see content in Table 2 hereinabove) supplemented with Par (150 mg $l^{-1}$) for 3 months with monthly transference to fresh media until embryogenic calli were formed. Embryogenic calli aggregates were transferred to RI medium (see content in Table 3 hereinabove) supplemented with Par (150 mg $l^{-1}$) and incubated for two months under 16/8 light/dark conditions, followed by an additional incubation period of 3-10 months in Par-supplemented (200 mg $l^{-1}$) R2 medium (see content in Table 3 hereinabove) with monthly transference to a fresh medium to promote Par-resistant (transformed) embryo germination. Germinated transformed embryos were rooted and developed into plantlets in Par-supplemented (200 mg $l^{-1}$) P1 medium (see content in Table 3 hereinabove) in Magenta boxes (Sigma).

Example 5

Genomic Integration and Expression of Exogenous Genes in pYC39-transformed Banana Plants Materials and methods:

DNA isolation: Genomic DNA was isolated from transformed and wild type banana leaves using a modified CTAB procedure (Bematzky and Tanksley, 1986; and Stewart and Via, 1993).

PCR analysis: PCR reaction mixture (11.5 µl) was composed of genormic DNA (1 µl), 2.5 mM dNTPs (1 µl each), primer DNA (0.25 µl of 20 pmol $\mu l^{-1}$ each), and Taq polymerase (JMR in the corresponding buffer; 0.1 µl). Full length nptII (700 bp fragment) was amplified using the primers 5'-GCC GCT TGG GTG GAG AGG CTA T-3' (SEQ ID NO: 6) and 5'-GAG GAA GCG GTC AGC CCA TTC-3' (SEQ ID NOs: 7). PCR reactions were hot-started (1 minute at 94° C.) and subjected to 30 cycles of: 30 seconds at 94° C.; 1 minute at 64° C.; and 2 minute at 72° C. The last extension phase was prolonged to 10 minutes at 72° C. Full length STS (1.2 kbp fragment) was amplified using the primers 5'-TGG GAT CAT GGC TTC AGT CGA GGA AAT TAG AAA CGC-3' (SEQ ID NO: 8) and 5'-CTT AAT TTG TCA CCA TAG GAA TGC TAT GC-3' (SEQ ID NO: 9). The PCR protocol used for STS amplification was as described above for nptII except that preheating was 5 min at 95° C. and the primer annealing temperature was 58° C.

Southern blot analysis: Genomic DNA was isolated from leaf samples of in vitro grown banana plants using a procedure essentially as described by Dellaporta et al. (1983). Genomic DNA (10 µg) was digested HindIII, electroporated in a 1% agarose gel and transferred to Hybond-XL blotting membrane (Amersham Pharmacia Biotech). A nptII specific probe was amplified from pGEM plasmid using the PCR protocol and hybridized at 55° C. The Hybridization signal was detected using the ECL detection kit (Amersham Biosciences).

Endochitinase activity measurement: Endochitinase activity was measured in leaf samples of transformed and wild type banana plants using the umbelliferyl fluorescence bioassay as described by Carsolio et al. (1994) and Kikkert et al. (2000). Briefly, leaf samples obtained from in vitro grown plantlets were ground in liquid nitrogen and extracted in a chitinase reaction buffer (50 mM sodium acetate buffer pH 5.0 with 15 mM β-mercaptoethanol). Leaf debris was removed by centrifugation at 13,000 and 4° C. for 15 minutes. The supernatant containing 10-20 µg total protein was mixed with 20-30 µl of 4-methylumbelliferyl β-D-N,N',N"-triacetyl-chitotriose (MUChT; Sigma; 240 µg/ml sodium acetate buffer). The mixture was incubated at 37° C. for 30 minutes and the enzymatic reaction was stopped after 20-30 minutes by adding 10 µl of 0.2 M $Na_2CO_3$ and by placing the mixture on crushed ice. The resulting fluorescence intensity of the reaction product, 4-methylumbelliferone (MU), was measured by a fluorometer and the fluorescence intensity value was converted to MU unit using a calibration curve constructed by MU standards (Sigma M-1381).

Results:

PCR analyses illustrated in FIGS. 2A-B demonstrated that genomic DNA obtained from transformed banana plants contained nptII and STS genes.

The integration of nptII gene in the genome of transformed banana plants was further confirmed by Southern blot analysis (FIG. 3).

Transformed banana plants positively expressed fungal endochitinase. Accordingly, as illustrated in FIG. 4, leaves of transformed banana plants exhibited 3.5 to 7 fold increase in endochitinase activity, as compared with wild-type plants.

These results confirmed that pYC39-transformed banana plants stably carry the nptII and STS genes in their genomes.

Example 6

Effect of Tissue Extract of pYC39-transformed banana plants on the germination of *Botrytis cinerea* spores in vitro Materials and methods:

*Botrytis cinerea* conidia: *Botrytis cinerea* was cultured on potato dextrose agar (Difco) and incubated for 14 days at 20° C. Conidia were then washed off from plates with sterile tap water and 0.01% Tween-80 and filtered through four layers of cheesecloth to remove mycelia residues. The conidia suspension was supplemented with 0.05% glucose and 0.05% $KH_2PO_4$ and the conidia density in suspension was adjusted to $1\times10^6$ cells/ml.

Spore germination bioassay: Leaves of transformed and wild type banana plants were extracted in 0.2 M $KH_2PO_4$ (pH 5.0) and were kept at −80° C. until used. A drop (20 µl) of conidia suspension and another drop (20 µl) of leaf extract were placed on a glass slide, mixed together and incubated at 20° C. and 100% R.H for 4 hours. Following incubation conidia were stained with aniline blue and observed for germination under a light microscope.

Results

As shown in Table 4 below, the germination incidence of *B. cinerea* conidia in leaf extracts obtained from transgenic banana lines averaged 22.9%, as compared with 53.2% in leaf extracts obtained from the wild-type plants. Similarly, the germ tube length of conidia germinating in the leaf extract of transgenic banana averaged 2.91 µm, as compared with 5.74 µm in the leaf extract of wild-type plants.

TABLE 4

Germination of *Botrytis cinerea* conidia in transgenic banana leaf extracts

| Banana line | Germination (%) | Germ tube length (µm) |
|---|---|---|
| 13.1 | 23 | 2.33 |
| 9.33 | 14.8 | 1.56 |
| 11.3 | 28 | 2.76 |
| 11.6 | 24.4 | 2.48 |
| 11.1 | 50.4 | 5.44 |
| WT-42.5 | 62 | 6.52 |
| WT-62.1 | 44.4 | 4.96 |

These results indicate that pYC39-transformed banana plants express disease-tolerance traits.

Example 7

Tolerance of pYC39-transformed Banana Plants to Leaf Spot Disease Caused by *Botrytis Cinerea*

Materials and Methods:

Six drops (about 20 µl each) of *B. cinerea* conidia suspension (prepared as described in Example 6 above) were inoculated onto banana leaves. The inoculated plants were placed in a transparent Perspex compartment in an illuminated growth chamber at 20-22° C. for 18 days. Disease severity was determined based on the size of lesions using a 12 mm diameter lesion as a base value of 100%. A pictorial scale was used to determine index severity values.

Results

As shown in Table 5 below, out of 10 different transgenic banana lines which were tested, 7 lines (9.3, 11.1,11.3, 11.6, 31.1 and 31.2) exhibited significantly reduced disease severity in at least one of two experiments, while 3 lines (9.3, 11.1 and 11.3) reduced disease severity in both experiments.

TABLE 5

*Botrytis cinerea* leaf spot severity in different transgenic banana lines

| Banana line | Exp 1 Incubation time (days) | | | Banana line | Exp 2 Incubation time (days) | | |
|---|---|---|---|---|---|---|---|
| | 8 | 14 | 18 | | 4 | 8 | 12 |
| 9.3 | 6.3 | 7.1* | 7.1* | 9.3 | 5* | 14.2* | 15* |
| 13.1 | 8.8 | 12.1 | 12.1 | 13.1 | 15.8 | 17.5 | 20 |
| 13.7 | 5.3 | 11.4 | 12.1 | 13.7 | 10* | 20 | 22.5 |
| 9.3 | 2.5* | 4.2* | 3.3* | 9.3 | 17.5 | 24.2 | 27.5 |
| 11.3 | 4.2 | 5.4* | 5.4* | 11.3 | 7.9* | 15.8* | 16.7* |
| 11.4 | 5 | 9.2 | 8.7 | 11.4 | 13.8 | 15.8* | 28.3 |
| 11.6 | 2.5* | 4.2* | 4.2* | 11.6 | 10.4* | 29.2 | 57.1 |
| 11.4 | 0* | 11.7 | 11.7 | 11.4 | 13.8 | 15* | 15.8* |
| 11.1 | 0* | 0* | 0* | 11.1 | 0* | 7.9* | 8.3* |
| 3.8 | 7.5 | 13.3 | 15 | 3.8 | 9.2* | 15.8* | 15.8* |
| 31.1 | 1.7* | 1.7* | 1.7* | 31.1 | 7.9* | 19.7 | 20.8 |
| 33.2 | 6.4 | 11.3 | 14.2 | 33.2 | 7.4* | 16.2* | 16.7* |
| WT | 3.8 | 8.7 | 9.2 | WT | 13.3 | 18.3 | 21.7 |
| LSD | 0.36 | 0.92 | 0.95 | LSD | 1.2 | 1.4 | 1.9 |

*significantly reduced disease severity as compared with the wild type control.

Hence, the results shown hereinabove demonstrate that banana plants can be successfully transformed with disease resistance genes and subsequently regenerated into mature plants expressing disease-resistant traits.

Example 8

Improved Tolerance Toward Black and Yellow Sigatoka Diseases (*Mycosphaerella* spp.) in Transgenic Cavendish Banana (*Musa* spp. AAA group) cv. 'Grand Nain'

Materials and Methods
Plasmid Transformation
The banana plants were transformed with PYC39 as described in Example 4 above.

Endochitinase activity measurement—The assay was effected as described in Example 5 above.

SOD activity assay—The assay was performed as described in Perl A, Perl-Treves R, Galili S, Aviv D, Shalgi E, Malkin S, and Galun E (1993). Enhanced oxidative stress defense in transgenic potato expressing tomato Cu, Zn superoxide dismutase. Thoer Appl Genet 85: 568-576.

STS assay—The assay was performed as described by Coutos-Thevenot P, Poinssot B, Bonomelli A, Yean H, Breda C, Buffard D, Esnault R, Hain R, Boulay M.(2001) In vitro tolerance to *Botrytis cinerea* of grapevine 41B rootstock in transgenic plants expressing the stilbene synthase Vst1 gene under the control of a pathogen-inducible PR 10 promoter. J Exp Bot 52: 901-910.

Banana infection and analysis—Plants were planted in duplicates in a random pattern including control non transgenic banana. Infection was done by natural spreading since the plantation was established in as Sigatoka natural habitat. Plants were not sprayed during growth and severity was evaluated by eye observation.

Results

Molecular characterization of transformants demonstrated that the transgenes had been stably integrated into the banana genome. Activity of the transgenes was assayed by endochitinase activity, SOD activity gels and Resveratrol levels in leaves of transgenic plants, indicating expression of the endochitinase gene, superoxide dismutase gene and stilbene gene respectively.

Table 6 below summarizes the results of activity expression.

TABLE 6

| Transgenic Designation | Endochitinae Activity | SOD Activity | Presence of Resveratrol | Sigatoka Severity |
| --- | --- | --- | --- | --- |
| Control | ND | ND | ND | 5 |
| 11.6 | + | + | ND | 2-3 |
| 31.1 | + | + | + | 1 |
| 13.1 | ND | + | + | 2-3 |
| 9.18 | ND | ND | + | 4 |
| 9.33 | + | ND | + | 2 |
| 11.3 | ND | ND | ND | 4-5 |
| 11.1 | + | + | + | 0-1 |
| 13.7 | + | ND | + | 2 |
| 9.32 | + | ND | + | 2-3 |
| 3.5 | ND | + | + | 2 |

Index
Sigatoka severity:
0—No symptoms observed
1—Mildsymptoms
2—Mild to moderate symptoms
3—Moderate symptoms
4—Moderate to severe symptoms
5—Severe symptoms
ND—not determined Notably, some transgenic plants expressed all three transgenes as was evident by analyzing activity and/or expression of the gene products of all three inserted genes (i.e., 31.1 and 11.1). Other plants expressed only one (9.18) or two (13.7, 9.32, 11.6) of the transgenes.

A clear correlation and synergism was evident between the tolerance to Sigatoka and the number of the genes expressed. The best transgenese (i.e. 31.1 and 11.1 FIG. 8b) expressed all three introduced genes and indeed exhibited the best protection against sigatoka. One transgene was found not to express any of the introduced genes (11.3 FIG. 8c) and the severity of the sigatoka symptoms in this plant was similar to control non transformed Grand Nain banana plants (FIG. 8a). Expression of two genes resulted in moderate protection (11.6 FIG. 8d) while expression of only a single provided only a limited protection level (i.e. 9.18).

These results clearly indicate a synergy in protection upon expression of two or even three gene products as compared to none or a single transgene expression (9.18 not shown).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with. specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

REFERENCES CITED (Additional references are cited hereinabove)

1. Becker D K, Dugdale B, Smith M K, Harding R M, Dale J L (2000) Genetic transformation of Cavendish banana (*Musa* spp. AAA group) cv. 'Grand Nain' via microprojectile bombardment. Plant Cell Rep 19: 229-234.

2. Bematzky R, Tanksley S D (1986) Methods for detection of single or low copy sequences in tomato on Southern blots. Plant Mol Biol Rep 4: 37-41.

3. Christensen, A. H., Quail, P. H. (1996) Ubiquitin promoter-based vectors for high-level expression of selectable and/or screenable marker genes in monocotyledonous plants. Trans. Res.5: 213-218

4. Côte FX, Domergue R, Monmarson S, Schwendiman J, Teisson C, Escalant J V (1996) Embryogenic cell suspensions from the male flower of *Musa* AAA cv. Grand nain. Physiol Plant 97: 285-290.

5. Dhed'a D, Dumortier F, Panis B, Vuylsteke D, De Langhe E (1991) Plant regeneration in cell suspension cultures of the cooking banana cv. 'Bluggoe' (*Musa* spp. ABB group). Fruits 46: 125-135.

6. Esca Jant J V, Teisson C (1989) Somatic embryogenesis and plants from immature zygotic embryos of the species *Musa acuminata* and *Musa balbisiana*. Plant Cell Rep 7: 665-668.

7. Escalant J V, Teisson C, Côte F X (1994) Amplified somatic embryogenesis from male flower of triploid banana and plantain cultivars (*Musa* sp.). In Vitro Cell Dev Biol 30: 181-186.

8. Georget F, Domergue R, Ferriere N, Côte F X (2000) Morphohistological study of the different constituents of a banana (*Musa* AAA, cv. Grande Naine) embryogenic suspension. Plant Cell Rep 19: 748-754.

9. Grapin A, Schwendiman J, Teisson C (1996) Somatic embryogenesis in plantain banana. In Vitro Cell Dev Biol 32: 66-71.

10. Hain R, Reif H J, Krause E, Langebartels R, Kindl H, Vornam B, Wiese W, Schmelzer E, Schreier P H, Stocker R H, Thomzik J E, Stenzel K (1993) Disease resistance results from foreign phytoalexin expression in a novel plant. Nature 361: 153-156.

11. Khalil S M, Cheah K T, Perez E A, Gaskill D A, Hu J S (2002) Regeneration of banana (*Musa* spp. AAB cv. Dwarf Brazilian) via secondary somatic embryogenesis. Plant Cell Rep 20: 1128-1134.

12. Kikkert J R, Ali G S, Wallace P G, Reisch B, Reustle G M (2000) Expression of a fungal chitinase in Vitis vinifera L. 'Merlot' and 'Chardonnay' plants produced by biolistic transformation. Acto Hort 528: 297-303.

13. Kosky R G, de Feria Silva M, Perez L P, Gilliard T, Martinez F B, Vega MR, Milian M C, Mendoza E Q (2002) Somatic embryogenesis of the banana hybrid cultivar FHIA-18 (AAAB) in liquid medium and scaled-up in a bioreactor. Plant Cell Tiss Org Culture 68: 21-26.

14. Lorito M, Harman G E, Hayes C K, Broadway R M, Tronsmo A, Woo S L, Di Pietro A (1993) Chitinolytic enzymes produced by *Trichoderma harzianum*: antifungal activity of purified endochitinase and chitobiosidase. Mol Plant Path 83: 302-307.

15. Marroquin C G, Paduscheck C, Escalant J V, Teisson C (1993) Somatic embryogenesis and plant regeneration through cell suspensions in *Musa acuminata*. In Vitro Cell Dev Biol 29: 43-46.

16. Mourichon X, Carlier J, Foure E (1997) Sigatoka leaf spot diseases—Black leaf streak disease (black Sigatoka), Sigatoka disease (yellow Sigatoka). *Musa* disease fact sheet No. 8.

17. Murashige T, Skoog F (1962) A revised medium for rapid growth and bioassay with tobacco tissue cultures. Physiol Plant 15: 473-497.

18. Navarro C, Ma Escobedo R, Mayo A (1997) In vitro plant regeneration from embryogenic cultures of a diploid and a triploid, Cavendish banana. Plant Cell Tiss Org Culture 51: 17-25.

19. Novak F J, Afza R, Van Duren M, Perea-Dallos M, Conger B V, Xiaolang T (1989) Somatic embryogenesis and plant regeneration in suspension cultures of dessert (AA and AAA) and cooking (ABB) bananas (*Musa* spp.). Biotechnology 7: 154-159.

20. Panis B, Wauwe A V, Swennen R (1993) Plant regeneration through direct somatic embryogenesis from protoplasts of banana (*Musa* spp.). Plant Cell Rep 12: 403-407.

21. Perl A, Perl-Treves R, Galili S, Aviv D, Shalgi E, Malkin S, Galun E (1993) Enhanced oxidative-stress defense in transgenic potato expressing tomato Cu, Zn superoxide dismutases. Theor Appl Genet 85: 568-576.

22. Sagi L, Panis B, Remy S, Schoofs H, De Smet K, Swennen R. Cammue BPA (1995) Genetic transformation of banana and plantain (*Musa* spp.) via particle bombardment. Bio/Technology 13:481-485

23. Sagi L, Remy S, Panis B, Swennen R, Volckaert G (1994) Transient gene expression in electroporated banana (*Musa* spp., cv. 'Bluggoe', ABB group) protoplasts isolated from regenerable embryogenetic cell suspensions. Plant Cell Rep 13: 262-266.

24. Schenk R U, Hildebrant A C (1972) Medium and techniques for induction and growth of monocotyledonous and dicotyledonous plant cell cultures. Can J Bot 50: 199-204.

25. Southern E (1975) Detection of specific sequences among DNA fragments separated by gel electrophoresis. J Mol Biol 98: 503-517.

26. Stewart C N, Via L E (1993) A rapid CTAB DNA isolation technique for RAPD fingerprint and other PCR applications. Biotechniques 14: 748-750.

27. Van Engelen (1995) pBINPLUS: an improved plant transformation vector based on pBIN19. Transgenic research 4: 288-290.

28. Wiese W, Vornam B, Krause E, Kindl H (1994) Structural organization and differential expression of three stilbene synthase genes located on a 13 kb grapevine DNA fragment. Plant Mol Biol 26: 667-677.

What is claimed is:

1. A banana cell comprising an endochitinase, a stilbene synthase and a superoxide dismutase, wherein said endochitinase is provided in SEQ ID NO: 1, said stilbene synthase is provided in SEQ ID NO: 2 and said superoxide dismutase is provided in SEQ ID NO: 3.

2. The banana cell of claim 1, wherein said endochitinase, stilbene synthase and superoxide dismutase are encoded from a nucleic acid construct which comprises an internal ribosome entry site sequence.

3. A banana plant comprising an endochitinase, a stilbene synthase and a superoxide dismutase, wherein said endochitinase is provided in SEQ ID NO: 1, said stilbene synthase is provided in SEQ ID NO: 2 and said superoxide dismutase is provided in SEQ ID NO: 3.

4. The banana plant of claim 3, wherein said endochitinase, stilbene synthase and superoxide dismutase are encoded from a nucleic acid construct which comprises an internal ribosome entry site sequence.

5. The banana cell of claim 1, wherein said endochitinase, stilbene synthase and superoxide dismutase confer resistance to sigatoka.

6. The banana plant of claim 3, wherein said endochitinase, stilbene synthase and superoxide dismutase confer resistance to Sigatoka.

* * * * *